(12) United States Patent
Nowak et al.

(10) Patent No.: US 11,071,519 B2
(45) Date of Patent: Jul. 27, 2021

(54) MEDICAL DEVICES, SYSTEMS AND METHODS FOR MONITORING AND STIMULATING OSTEOGENESIS

(71) Applicant: ORTHOFORGE, Grand Rapids, MI (US)

(72) Inventors: Brent Nowak, Ada, MI (US); Erik Hall, East Grand Rapids, MI (US)

(73) Assignee: Orthoforge, Inc., Grand Rapids, MI (US)

( * ) Notice: Subject to any disclaimer, the term of this patent is extended or adjusted under 35 U.S.C. 154(b) by 406 days.

(21) Appl. No.: 15/351,324

(22) Filed: Nov. 14, 2016

(65) Prior Publication Data

US 2017/0135671 A1    May 18, 2017

Related U.S. Application Data

(60) Provisional application No. 62/254,892, filed on Nov. 13, 2015.

(51) Int. Cl.
*A61B 8/08* (2006.01)
*A61B 5/00* (2006.01)
(Continued)

(52) U.S. Cl.
CPC .......... *A61B 8/0875* (2013.01); *A61B 5/0059* (2013.01); *A61B 5/4504* (2013.01); *A61B 6/505* (2013.01); *A61B 8/4227* (2013.01); *A61B 8/5223* (2013.01); *A61N 7/00* (2013.01); *A61B 5/05* (2013.01); *A61B 5/4842* (2013.01);
(Continued)

(58) Field of Classification Search
CPC ......... A61B 8/485; A61B 8/12; A61B 5/0031; A61B 5/4504; A61B 8/0875; A61B 8/5284; A61B 8/5292; A61B 8/5269; A61B 8/5223; A61B 8/5207; A61B 5/4842;
(Continued)

(56) References Cited

U.S. PATENT DOCUMENTS 4,530,360 A    7/1985   Duarte
4,774,959 A  * 10/1988  Palmer ................. A61B 8/0875
                                                        600/442
(Continued)

FOREIGN PATENT DOCUMENTS

CN    105534549 A1    5/2016
DE    102010053449 A1  6/2012
(Continued)

OTHER PUBLICATIONS

Chaffai, S. et al. "In vitro measurement of the frequency-dependent attenuation in cancellous bone between 0.2 and 2 MHz". The Journal of the Acoustical Society of America. 108, 1281(2000) (Year: 2000).*

(Continued)

*Primary Examiner* — Bill Thomson
*Assistant Examiner* — Helene Bor
(74) *Attorney, Agent, or Firm* — Thompson Hine LLP

(57) ABSTRACT

Devices, systems and/or methods for monitoring and/or stimulating osteogenesis use sensor data from a target site of a bone to produce a quantitative output that can be used to determine the healing rate of the patient, when the bone at the target has fully consolidated and/or to direct further treatment of the patient.

16 Claims, 30 Drawing Sheets

(51) Int. Cl.
*A61B 8/00* (2006.01)
*A61N 7/00* (2006.01)
*A61B 5/05* (2021.01)
*A61B 6/00* (2006.01)

(52) U.S. Cl.
CPC ............ *A61B 8/485* (2013.01); *A61B 8/5207* (2013.01); *A61N 2007/0013* (2013.01); *A61N 2007/0052* (2013.01)

(58) Field of Classification Search
CPC .. A61B 5/05; A61B 6/05; A61B 6/505; A61N 7/00; A61N 2007/0013
USPC .............................................. 706/20, 22, 24
See application file for complete search history.

(56) References Cited

U.S. PATENT DOCUMENTS

| | | | |
|---|---|---|---|
| 5,143,069 A * | 9/1992 | Kwon ................ | A61B 8/0875 600/437 |
| 5,496,256 A | 3/1996 | Bock et al. | |
| 5,613,493 A | 3/1997 | Schafer et al. | |
| 5,706,815 A | 1/1998 | Sarvazyan et al. | |
| 5,717,142 A | 2/1998 | Schafer et al. | |
| 5,904,659 A * | 5/1999 | Duarte ................ | A61N 7/00 601/2 |
| 5,908,388 A * | 6/1999 | Watkin ................ | A61B 8/0858 600/438 |
| 6,012,332 A | 1/2000 | Schafer et al. | |
| 6,029,522 A | 2/2000 | Schafer et al. | |
| 6,092,418 A | 7/2000 | Schafer et al. | |
| 6,213,958 B1 | 4/2001 | Winder | |
| 6,276,209 B1 | 8/2001 | Schafer et al. | |
| 6,457,363 B1 | 10/2002 | Schafer et al. | |
| 6,468,215 B1 * | 10/2002 | Sarvazyan ........... | A61B 8/0875 600/438 |
| 7,112,173 B1 | 9/2006 | Kantorovich et al. | |
| 7,410,469 B1 | 8/2008 | Talish et al. | |
| 7,601,120 B2 | 10/2009 | Moilanen et al. | |
| 7,611,465 B2 | 11/2009 | Antich et al. | |
| 7,938,777 B2 | 5/2011 | Amiot et al. | |
| 9,301,729 B2 | 4/2016 | Sakamoto et al. | |
| 9,445,720 B2 | 9/2016 | Janna et al. | |
| 9,846,938 B2 | 12/2017 | Steigauf et al. | |
| 2002/0032393 A1 | 3/2002 | Talish et al. | |
| 2002/0161300 A1 | 10/2002 | Hoff et al. | |
| 2003/0153848 A1 * | 8/2003 | Talish ................ | A61B 17/1677 601/2 |
| 2004/0249580 A1 * | 12/2004 | Pourcelot ................ | A61B 8/08 702/43 |
| 2005/0075846 A1 * | 4/2005 | Kim ..................... | G01N 29/245 703/1 |
| 2006/0235424 A1 | 10/2006 | Vitale et al. | |
| 2008/0097211 A1 * | 4/2008 | Sarvazyan ........... | A61B 8/0875 600/449 |
| 2009/0131838 A1 | 5/2009 | Fotiadis et al. | |
| 2009/0156969 A1 | 6/2009 | Santangelo | |
| 2011/0224545 A1 | 9/2011 | Nakamura et al. | |
| 2012/0191159 A1 * | 7/2012 | Willeford ................ | A61N 7/00 607/51 |
| 2012/0253196 A1 | 10/2012 | Nagata et al. | |
| 2013/0138017 A1 * | 5/2013 | Jundt .................... | A61B 17/66 601/2 |
| 2013/0245443 A1 * | 9/2013 | Karjalainen ......... | A61B 8/0875 600/438 |
| 2014/0155748 A1 * | 6/2014 | Pernisa ................ | G06T 7/0012 600/443 |
| 2015/0359478 A1 | 12/2015 | Eyal et al. | |

FOREIGN PATENT DOCUMENTS

| | | |
|---|---|---|
| WO | 9945348 A1 | 9/1999 |
| WO | 2011119873 A2 | 9/2011 |
| WO | 2015113813 A1 | 8/2015 |

OTHER PUBLICATIONS

Eun Kyu Lee, International Search Report, dated Jan. 10, 2017, 10 pages, Republic of Korea.
Extended European Search Report, European Patent Application No. 16865247.7, dated Apr. 29, 2019.
Wikipedia, "Bone fracture", https://en.wikipedia.org/wiki/Bone_fracture, downloaded Feb. 18, 2019, 13 pages.
Kabir, M. F., et al., "Classifying Defects in Pallet Stringers by Ultrasonic Scanning", Wood and Fiber Science 35(3), 2003, 341-350.
Kabir, M. F., et al., "Detection of Defects in Red Oak Deckboards by Ultrasonic Scanning", Proceedings in 4th International Conference on Image Processing and Scanning of Wood, Aug. 21-23, 2000, 89-96.
Kabir, M. F., et al., "Time Domain Ultrasonic Signal Characterization for Defects in Thin Unsurfaced Hardwood Lumber", Wood and Fiber Science, 34(1), 2002, 165-182.
Chachan, et al., "Ultrasound Monitoring of Fracture Healing", Journal of Orthopaedic Trauma: Mar. 2015, vol. 29, Issue 3, p. e133-e138.
Protopappas, et al., "Ultrasonic monitoring of bone fracture healing," in IEEE Transactions on Ultrasonics, Ferroelectrics, and Frequency Control, vol. 55, No. 6, pp. 1243-1255, Jun. 2008.
Milan et al., "Ultrasonic Study of Normal and Fractured Bone", Clinical Orthopaedics and Related Research (1976-2007): Sep. 1975—vol. 111, p. 175-180.
Schmid et al., "The Investigation of Suspected Fracture—a Comparison of Ultrasound With Conventional Imaging", Dtsch Arztebl Int. 2017;114(45):757-764.
Claes, L.E., Cunningham, J.L., "Monitoring the Mechanical Properties of Healing Bone", Clin Orthop Relat Res 467, 1964-1971 (2009).
Eastaugh-Waring, S.J., Joslin, C.C., Hardy, J.R.W. et al. Quantification of Fracture Healing from Radiographs Using the Maximum Callus Index. Clin Orthop Relat Res 467, 1986-1991 (2009).
Potsika et al., "Application of an effective medium theory for modeling ultrasound wave propagation in healing long bones", Ultrasonics, vol. 54, Issue 5, Jul. 2014, pp. 1219-1230.
Malo et al., "Numerical Analysis of Uncertainties in Dual Frequency Bone Ultrasound Technique", Ultrasound in Medicine & Biology, vol. 36, Issue 2, Feb. 2010, pp. 288-294.
Wear et al., "Quantitative Ultrasound and the Management of Osteoporosis", Acoustics Today, Summer 2018, vol. 14, issue 2, p. 34.

* cited by examiner

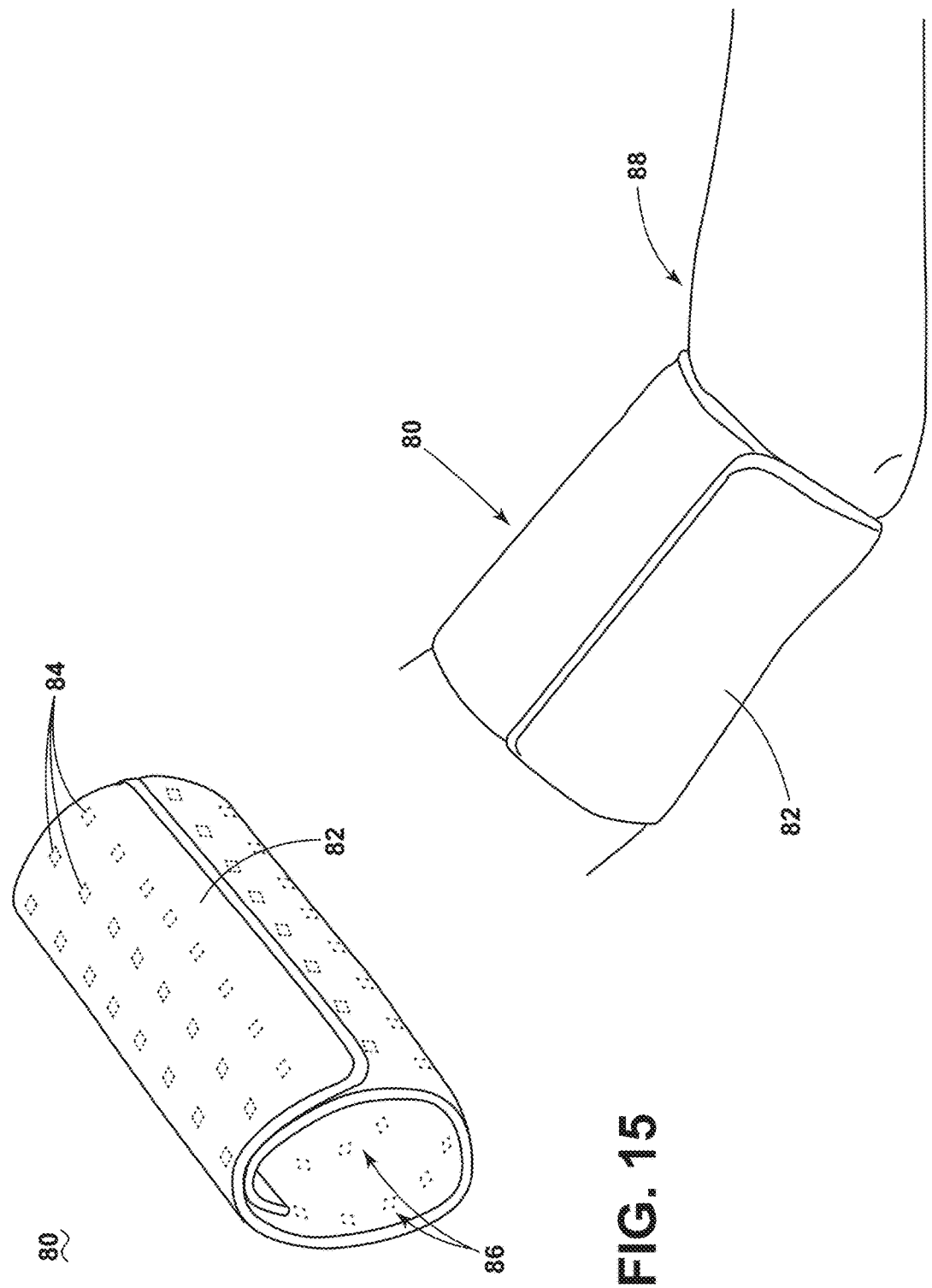

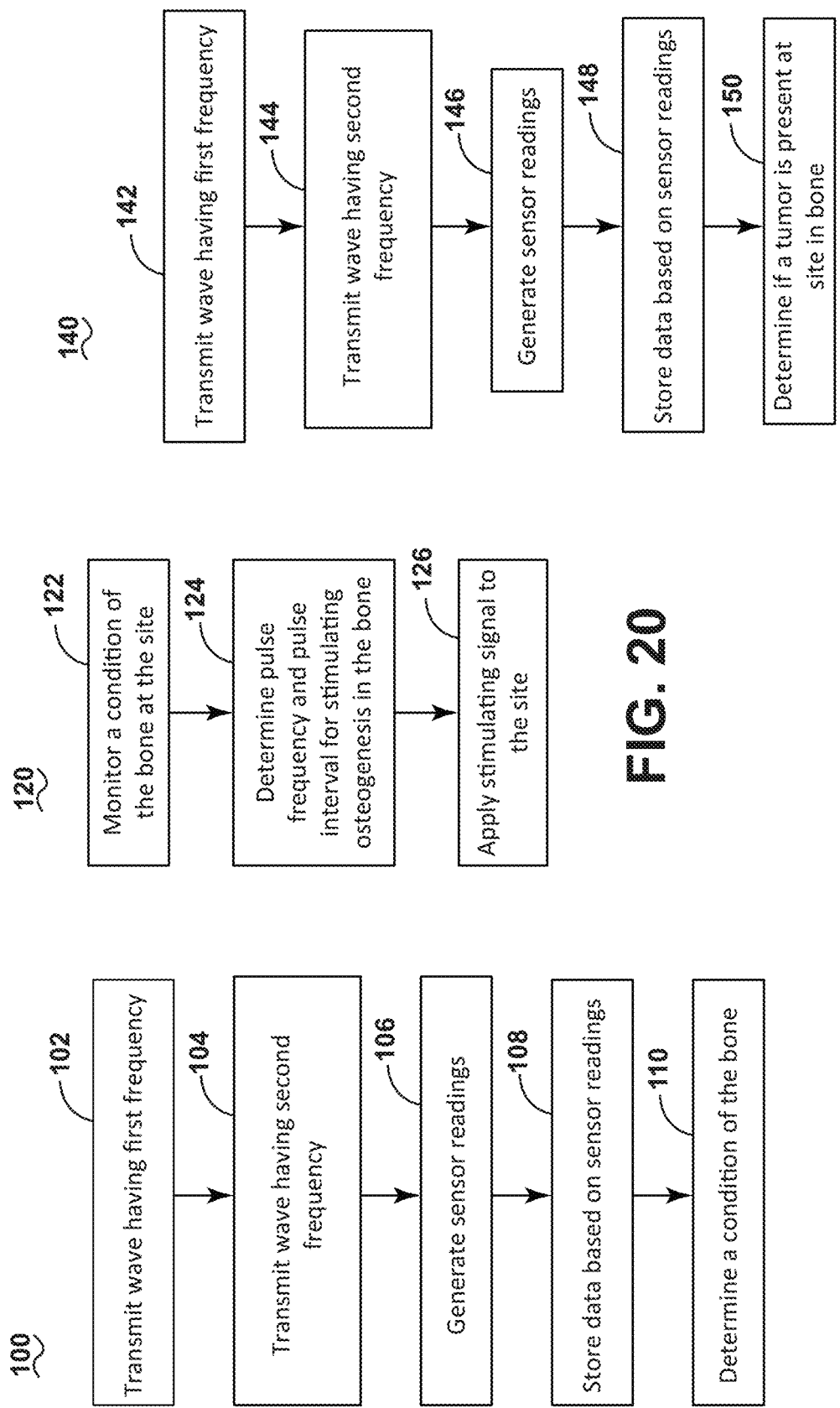

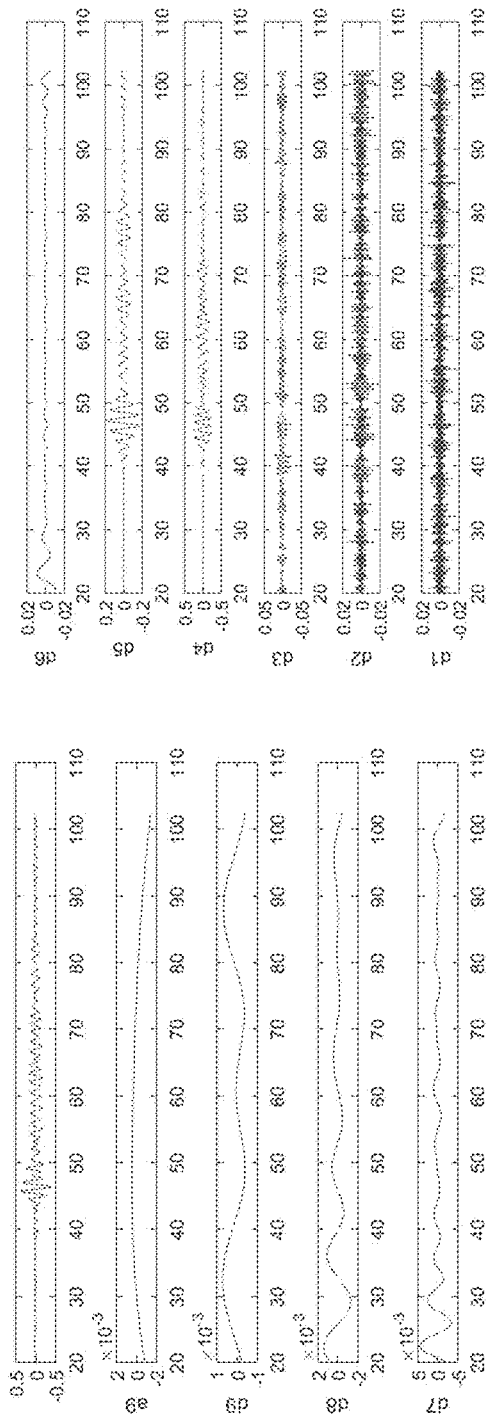
Figure 30: Wavelets for AP TxRx 014 2dB
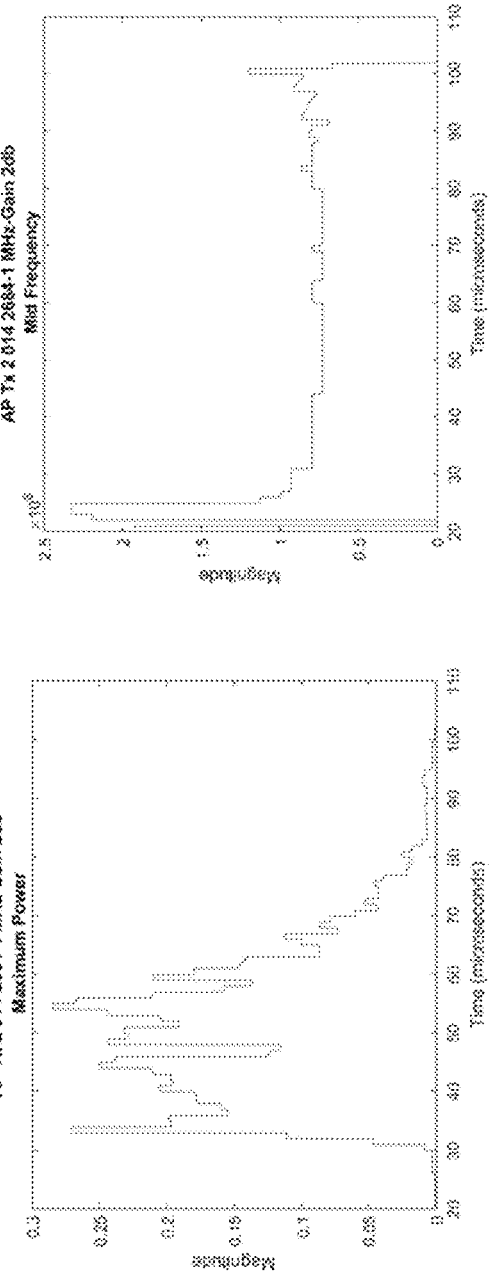
Figure 31: Maximum Power and Mid Frequency of 15 microsecond moving windows for AP TxRx 014 2dB

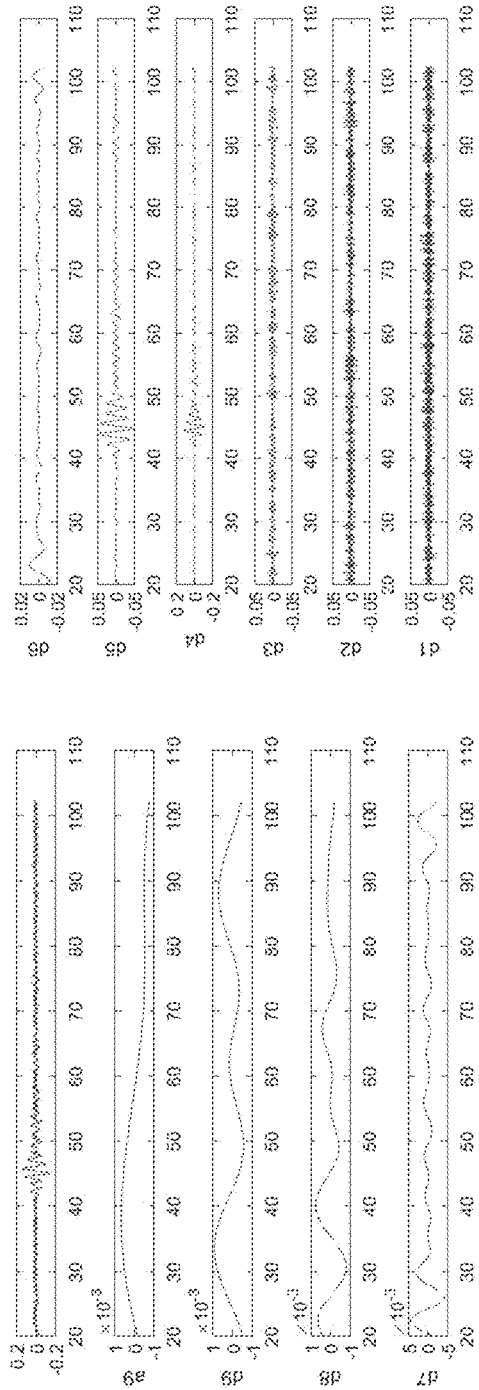
Figure 32: Wavelets for AP TxRx 035 2684
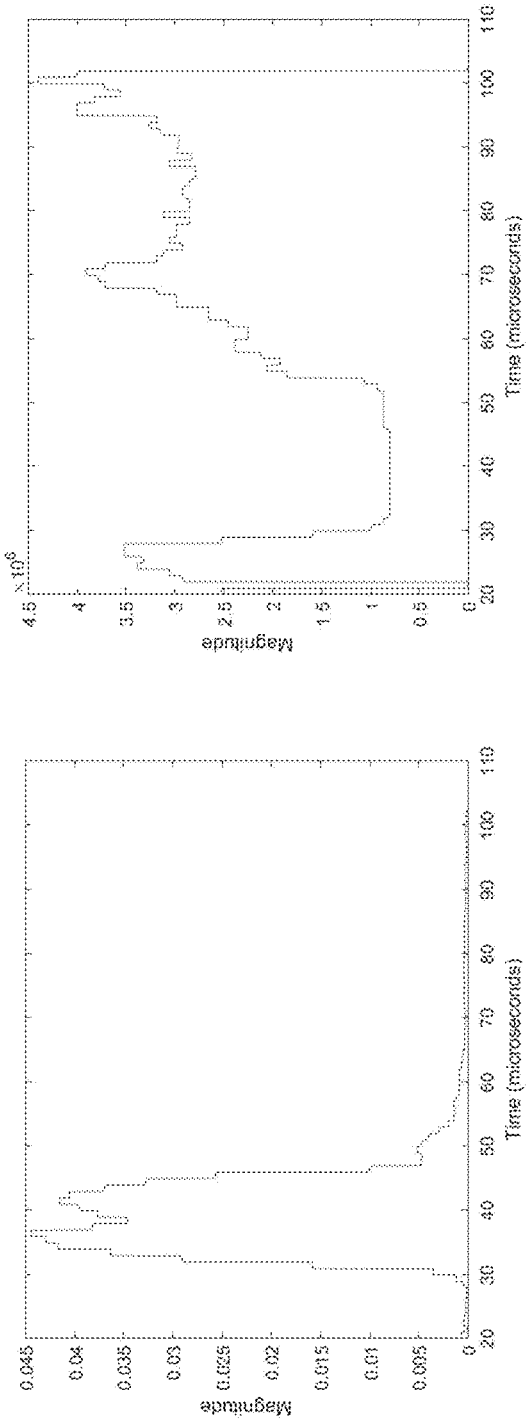
Figure 33: Maximum Power and Mid Frequency of 15 microsecond moving windows for AP TxRx 035 2684
AP Tx 1 035 2684-1 MHz-Gain -1dbMaximus
AP Tx 1 035 2684-1 MHz-Gain -1dbMid Fre

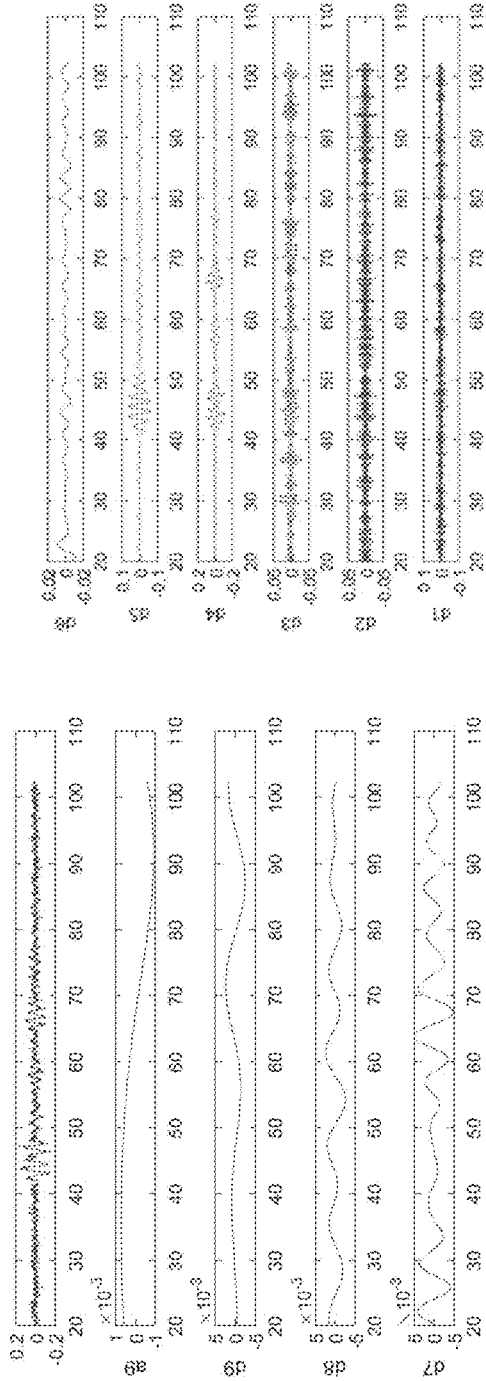
Figure 34: Wavelets for AP TxRx 035 2684 -7dB
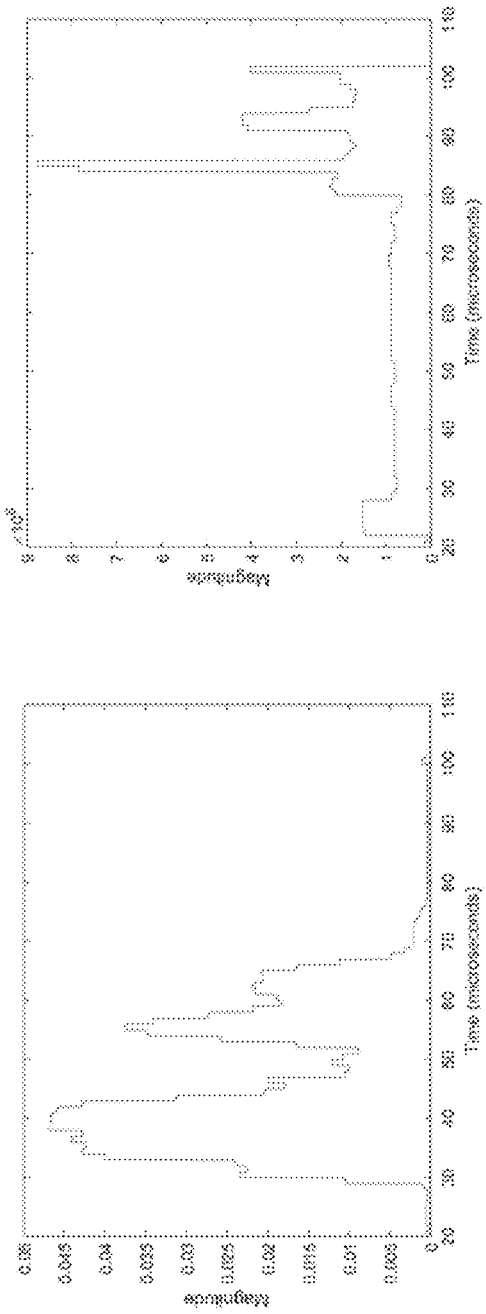
Figure 35: Maximum Power and Maximum Frequency of 15 microsecond moving windows for AP TxRx 035 2684 -7dB

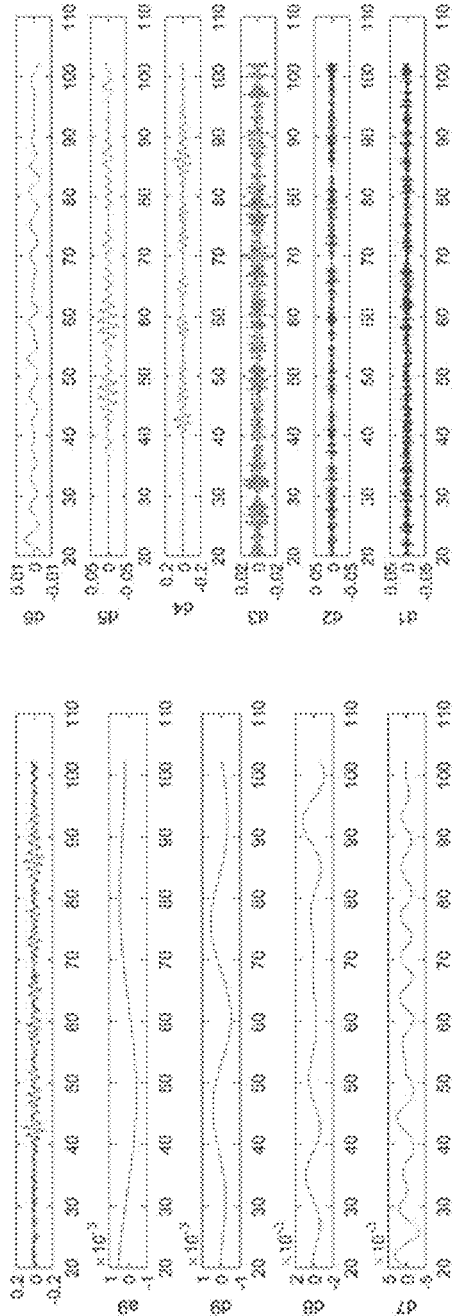
Figure 36: Wavelets for AP TxRx 021 2684 -1dB
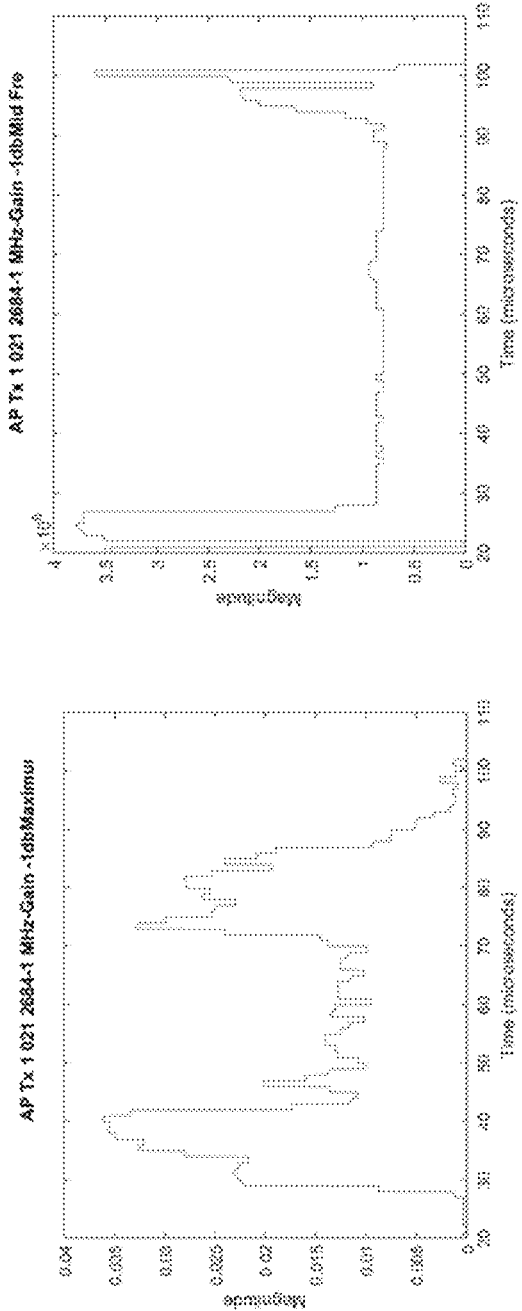
Figure 37: Maximum Power and Mid Frequency of 15 microsecond moving windows for AP TxRx 021 2684 -1dB

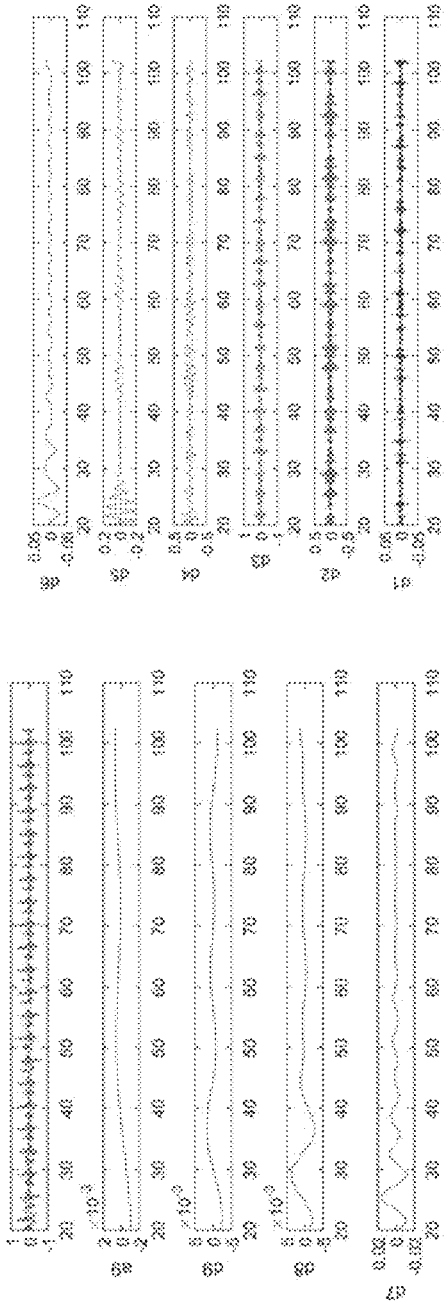
Figure 38: Wavelets for ML TxRx 056 2684 11dB
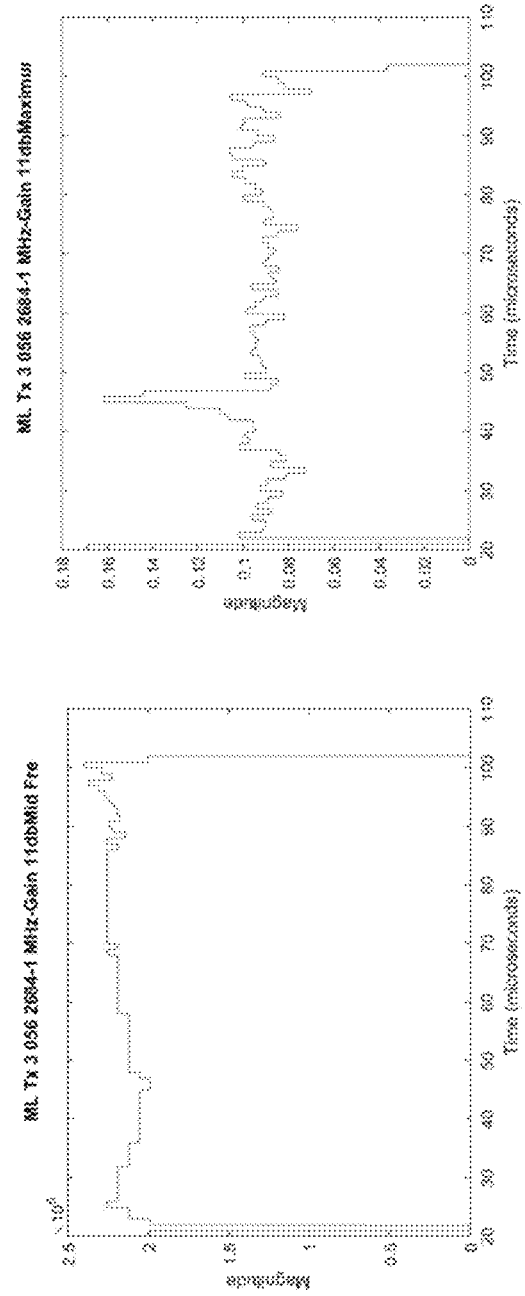
Figure 39: Maximum Power and Mid Frequency of 15 microsecond moving windows for ML TxRx 056 2684 11dB

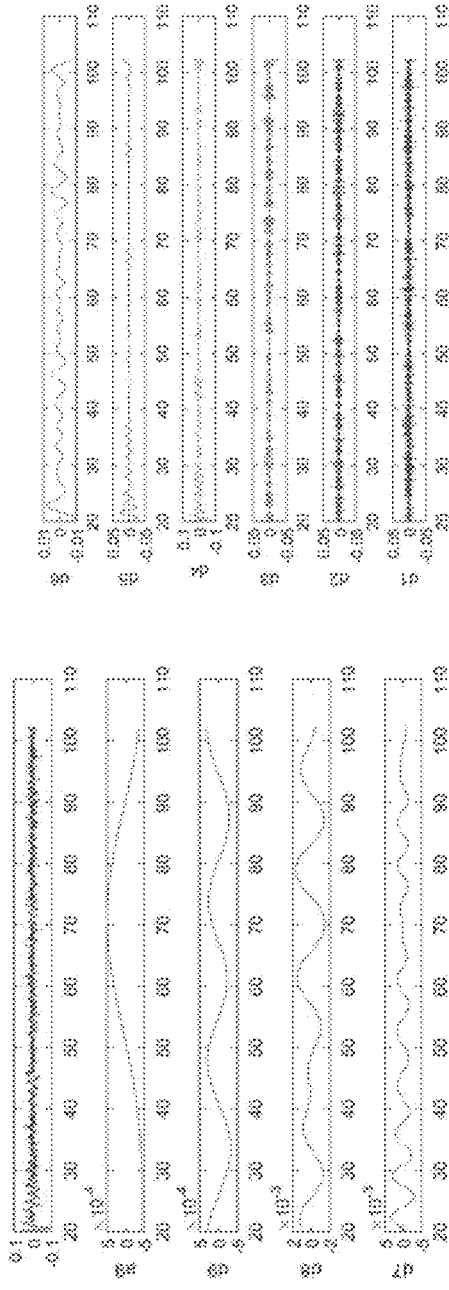
Figure 40: Wavelets for ML TxRx 042 2684 -1dB
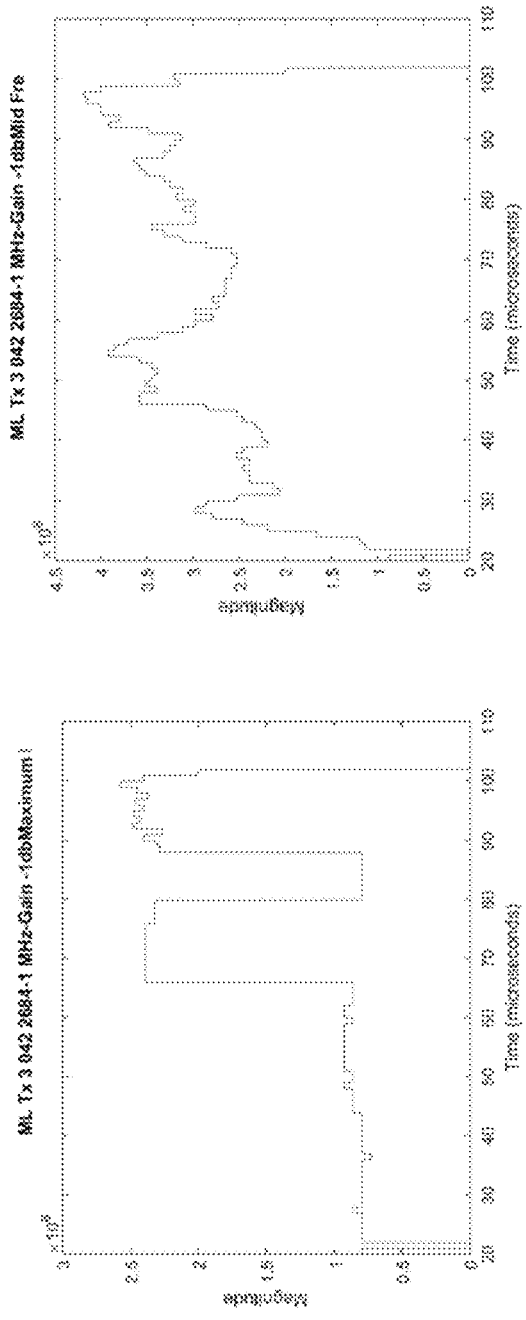
Figure 41: Maximum Frequency and Mid Frequency of 15 microsecond moving windows for ML TxRx 042 2684 -1dB

MEDICAL DEVICES, SYSTEMS AND METHODS FOR MONITORING AND STIMULATING OSTEOGENESIS

CROSS-REFERENCE TO RELATED APPLICATION(S)

This application claims the benefit of U.S. Provisional Application No. 62/254,892, filed Nov. 13, 2015, which is incorporated herein by reference in its entirety.

BACKGROUND OF THE INVENTION

Osteogenesis is the formation and development of bony tissue. After a fracture due to an unintentional wound, like a traumatic break, or an intentional wound due to surgery or other medical treatment, a bone will undergo osteogenic healing. There are three major phases of fracture healing, including a reactive phase, a reparative phase, and a remodeling phase. These can be further sub-divided into five stages: a fracture and inflammatory phase in which a hematoma forms, granulation tissue formation in which a soft callus forms, cartilage callus formation in which a hard callus forms, lamellar bone deposition in which bone forms, and remodeling to the original contour or bone consolidation. The rate, quality, and time for healing vary from patient to patient.

Currently, bone healing is assessed qualitatively using X-ray or another imaging technique, or through external palpations. These methods are subjective, and the accuracy of the assessment is dependent on the experience and skill of the medical practitioner. The X-ray and palpation assessments are subjective and suffer from interpretation, rather than a quantitative measurement.

For example, once a hard callus begins to form, an X-ray may not be reliable because the hard callus will appear as consolidated bone, even if the entire fracture site is not fully consolidated. A bone that heals asymmetrically may appear healed (i.e. fully consolidated) on one X-ray, but another X-ray taken at a different angle may reveal that fracture still exists.

Osteogenesis stimulation is a medical treatment that enhances and/or activates the natural healing process of bone. This treatment requires a stimulation device that sends pulses of acoustic or electromagnetic energy to a site within the bone. Treatment schemes are fixed regimens that do not vary from patient to patient. Osteogenesis formation may be enhanced by the introduction of biologic and/or pharmacologic drugs/medicines with or without the inclusion of scaffolding that may or may not be coated with additional or alternate biologic and/or pharmacologic drugs/medicines. Alternately, osteogenesis formation may be enhanced by devices understood in the practice as distraction osteogenesis systems that enable additional bone formation to grow that replaces lost bone due to accidents or modification of the bone due to pathologies, such as but not limited to, genetic causes, pseudo-arthrosis of long bones, limb lengthening, joint arthrodesis, and the like. These distraction osteogenesis devices may be external, such as but limited to, Illizarov Devices and Taylor Spatial Frames or the like. Alternate distraction osteogenesis devices may be internal, such as but not limited to, intra-medullary nails. In all cases of bone formation, reformation, or stimulation no devices exist that quantitatively measure and report the state, condition, or rate of bone healing.

BRIEF DESCRIPTION OF THE INVENTION

The invention relates to devices, systems and/or methods for monitoring and reporting on all phases of the healing process, with or without stimulating osteogenesis, pharmacology, biologics, or other interventions. In one aspect, the invention relates to devices, systems and/or methods for monitoring and/or stimulating osteogenesis that use sensor data from a target site on a bone to produce a quantitative output.

In one aspect, a method of monitoring a bone using a percutaneous monitoring device having multiple sensors applied to the body of a patient, wherein the multiple sensors are adjacent a target site of the bone is provided, comprising the steps of: transmitting, from one of the multiple sensors of the monitoring device, at least one wave to the target site; receiving, by one of the multiple sensors of the monitoring device, the at least one wave to generate sensor readings; storing data based on the sensor readings; and quantifying a condition of the target site of the bone from the data based on sensor readings, wherein the at least one wave comprises a frequency in a range of 0.7 MHz-3.0 MHz.

In another aspect, a percutaneous bone monitoring system comprises a percutaneous bone monitoring device adapted to be applied to the body of a patient, the device comprising a plurality of sensors, at least one of the sensors comprising a transmitter capable of transmitting a wave, and at least one of the sensors comprising a receiver capable of receiving the transmitted wave and creating a signal representative of a received wave, and a controller operably coupled with the device and comprising a central processing unit and a memory, wherein the controller is configured to transmit at least one wave from the transmitter to a target site of the bone, receive the at least one wave by the receiver to generate sensor readings, store data based on the sensor readings in the memory, and quantifying a condition of the bone at the target site from the data based on sensor readings, wherein the at least one wave comprises a frequency in a range of 0.7 MHz-3.0 MHz.

BRIEF DESCRIPTION OF THE DRAWINGS

In the drawings:

FIG. 15 is an illustration of another embodiment of a bone monitoring and/or stimulation device;

FIG. 16 illustrates the device of FIG. 15 on an arm of a patient;

FIG. 19 is a flow chart illustrating a multi-frequency method of monitoring a bone;

FIG. 20 is a flow chart illustrating a method of stimulating osteogenesis in a bone;

FIG. 21 is a flow chart illustrating a method of identifying and diagnosing a tumor in a bone;

FIG. 30 illustrates wavelets for an anterior-to-posterior (AP) transmission path and TxRx sensor modality of a sheep at day 14 of healing for one embodiment of a wavelet algorithm that may be used with the devices, systems, and methods described herein;

FIG. 31 illustrates moving windows for power spectrum analysis for the AP/TxRx modality from FIG. 30;

FIG. 32 illustrate another example of wavelets for an AP/TxRx modality of a sheep at day 35 of healing for one embodiment of a wavelet algorithm that may be used with the devices, systems, and methods described herein;

FIG. 33 illustrates moving windows for power spectrum analysis for the AP/TxRx modality FIG. 32;

FIG. 34 illustrate another example of wavelets for an AP/TxRx modality of a sheep at day 35 of healing for one embodiment of a wavelet algorithm that may be used with the devices, systems, and methods described herein;

FIG. 35 illustrates moving windows for power spectrum analysis for the AP/TxRx modality from FIG. 34;

FIG. 36 illustrate another example of wavelets for an AP/TxRx modality of a sheep at day 21 of healing for one embodiment of a wavelet algorithm that may be used with the devices, systems, and methods described herein;

FIG. 37 illustrates moving windows for power spectrum analysis for AP/TxRx modality from FIG. 36;

FIG. 38 illustrate another example of wavelets for a medial-to-lateral (ML) transmission path and TxRx sensor modality of a sheep at day 56 of healing for one embodiment of a wavelet algorithm that may be used with the devices, systems, and methods described herein;

FIG. 39 illustrates moving windows for power spectrum analysis for the ML/TxRx modality from FIG. 38;

FIG. 40 illustrate another example of wavelets for a ML/TxRx modality of a sheep at day 42 of healing for one embodiment of a wavelet algorithm that may be used with the devices, systems, and methods described herein; and FIG. 41 illustrates moving windows for power spectrum analysis for the ML/TxRx modality from FIG. 40.

DESCRIPTION OF EMBODIMENTS OF THE INVENTION

Figure 1:
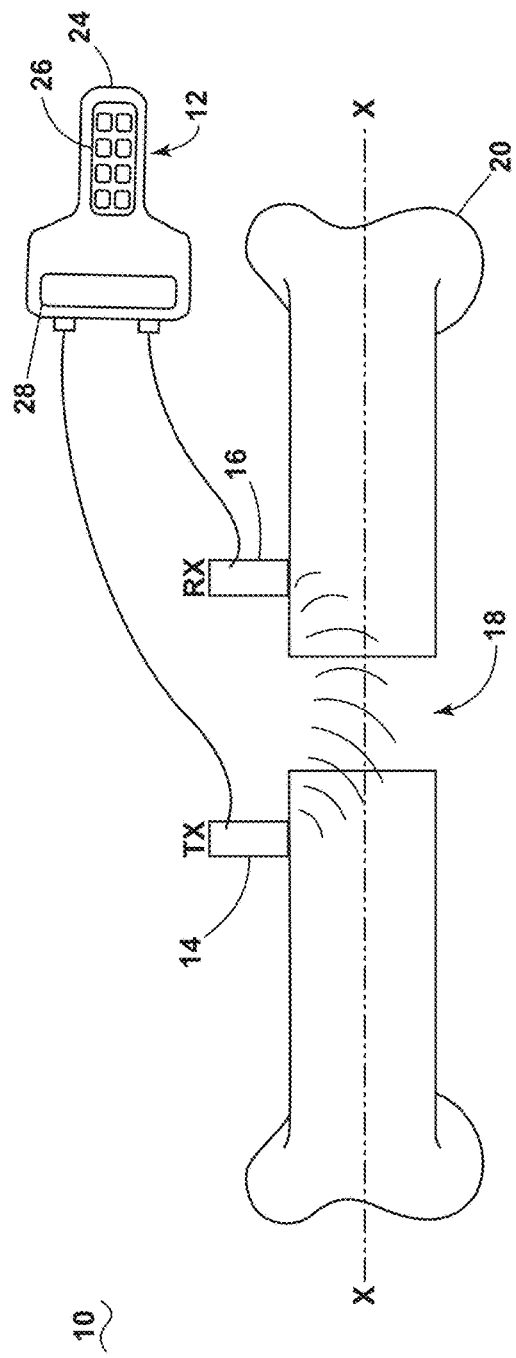
FIG. 1 is a schematic diagram of a system for monitoring osteogenesis using a transmit-receive sensor modality relative to a target site in a bone, including a controller and sensors positioned in a longitudinal transmission orientation relative to a target site in a bone.

The described embodiments of the present invention are directed to devices, systems and methods for monitoring and/or stimulating osteogenesis. It will be understood that the monitoring and/or stimulating of osteogenesis will be across all phases/stages of healing that includes, but is not limited to, the hematoma, soft callus, hard callus, cortical bone and any other intermediate physiology. That is, the use of the word bone within includes but is not limited to hematoma, soft callus, hard callus, cortical bone and any other intermediate physiology. Some other examples include necrosis, tumor, or other pathological condition of the physiology.

For purposes of illustration, the present invention will be described with respect to a human patient. It will be understood, however, that the invention is not so limited and may have general applicability in animals as well.

Embodiments of the present invention use measurements taken at a target site of a bone to characterize a condition of the bone, including, but not limited to, internal body healing rates/trends or the healing stage of the bone. This provides a quantitative output that can be used to determine healing progress within each phase of fracture healing that can be defined by the absolute bone formation and/or the healing trend (e.g. rate) and/or rate of change of the healing trend (e.g. inflection points); between phases; and/or when a bone has fully consolidated and/or to direct further treatment of the patient. Using the devices, systems, and/methods of the embodiments of the invention disclosed therein, a patient's treatment can be directed by their own personal healing rate. The use of casts and external fixators can be implemented for an individual's needs, rather than according to general standards. The use of X-Rays can be greatly reduced or eliminated.

Embodiments of the present invention can be used after a fracture or break due to injury, or after a surgical procedure involving cutting or breaking a bone (ex: osteotomy or corticotomy). Embodiments of the present invention may present a 360 degree view of the target site, which may benefit target sites that heal asymmetrically. Bone fragments can also be located in a patient using at least some embodiments of the present invention.

The various embodiments of devices, systems, and methods disclosed herein may be embodied in a diagnostic tool for use in a medical setting (hospital, clinic, etc.) by a clinician or medical practitioner, or at home, where the diagnostic tool is operated by the patient or another non-clinician. In either mode of operation, the diagnostic tool provides data to a clinician, who makes a diagnosis based on the data. The diagnostic tool can be an ex vivo device that does not require any invasive treatment of the patient, and can be applied or mounted on the patient's skin such that the acoustic transmission is percutaneous.

In some applications, the devices, systems, and methods may be applied to distraction or bone regeneration procedures. The various embodiments of devices, systems, and methods disclosed herein may monitor the bone restoration process and reports the condition and trends for all such distraction osteogenesis devices, drugs/medicines used to enhance osteogenesis formation, and the like.

The various embodiments of devices, systems, and methods disclosed herein may also be used for osteogenesis stimulation procedures. Such stimulation procedures can induce new bone growth and formation at a target site.

The various embodiments of devices, systems, and methods disclosed herein may also be used to aid in diagnosis and treatments for osteonecrosis and orthopedic oncology, and wound monitoring in general, including the location or tumors or other bone growths.

As used herein, the term "user" includes, but is not limited to, physicians and other medical professionals, as well as the patient being treated or monitored, unless otherwise noted.

FIG. 1 is a schematic diagram of a system 10 for monitoring osteogenesis, including a controller 12 and sensors 14, 16 positioned in a longitudinal transmission orientation relative to a target site 18 in a bone 20. The target site 18 may be a fracture, osteotomy, cortectomy, tumor, or another site of interest in or on the bone. The sensors 14, 16 are configured to determine at least one physical characteristic of the bone 20. The sensors 14, 16 can be placed internally, on the bone 20, or externally, i.e. on the skin. In one example, the sensors 14, 16 can be placed under or on a fixator. The controller 12 can be electromechanical, hydraulic-mechanical, pneumatic-mechanical with or without micro-electronic control. The sensors 14, 16 may be acoustic sensors; alternate and/or complementary sensors include, but are not limited to, capacitive, inductive, magnetic, thermal, Hall Effect, piezoelectric and other electromagnetic sensors, as well as, chemo-electromagnetic sensors such as but not limited to, pH, salinity, temperature, or other biological or physiologic sensing modality. These sensing modalities may be employed separately or in conjunction with other modes.

At least one of the sensors 14 can be a transmitter (Tx), while another sensing element 16 can be a receiver (Rx). The sensors 14, 16 may also be transceivers (transmitter/receivers), and the controller 12 may control the sensors 14, 16 to operate as transmitters, receivers, or both. Examples of the sensors 14, 16 include, but are not limited to, ultrasound, inductive, capacitive, electromagnetic, magneto-resistive, magneto-restrictive, and piezoelectric sensors, including transceivers or transducers. In this regard, the sensors 14, 16 can function as a load condition sensor which measures not only field intensity but reflection, which is used with a control system as described below. Sound waves reflect, refract, diffract, and/or are transmitted as they encounter changes in material properties associated with bone, callus (soft and hard), fat, muscle, bone fragments, tumors, and/or necrotic tissue; the analysis of the present invention is sophisticated and can take all of these factors into account.

The sensor 14, 16 can, for example, measure changes in the elastic deformation of the healing region using a light, magnetic field, or electromagnetic receiving sensor. Additionally, the sensor 14, 16 can measure the change in inductance, or reluctance of the healing region using a magnetic field induced through the healing region. Induction of the magnetic field can include the use of coils formed onto a flexible circuit board and can include a mechanism for directing the magnetic field such as mu-metal shielding.

In FIG. 1, the sensors 14, 16 are provided in a longitudinal transmission orientation relative to the target site 18 in the bone 20. In longitudinal transmission, one sensing element, designated in this embodiment as a transmitter (Tx) 14, is positioned on a first side of the target site 18 and another sensing element, designated in this embodiment as a receiver (Rx) 16, is positioned on a second or opposite side of the target site 18 along the longitudinal axis X of the bone 20. During operation, the transmitter 14 can transmit a wave to the receiver 16 along the longitudinal axis X of the bone 20. The transmitter 14 can include a current responsive fault limiter which controls the application of energy into the healing region of the target site 18. Additionally, the signal emitted from the transmitter 14 can be focused onto particular regions of the healing region. For example, a material having a thinned region which allows masking of the transmitted signal can be positioned between the transmitter 14 and the healing region of the bone 20. Optionally, wave guides can be employed to focus the transmitter energy.

Figure 2:
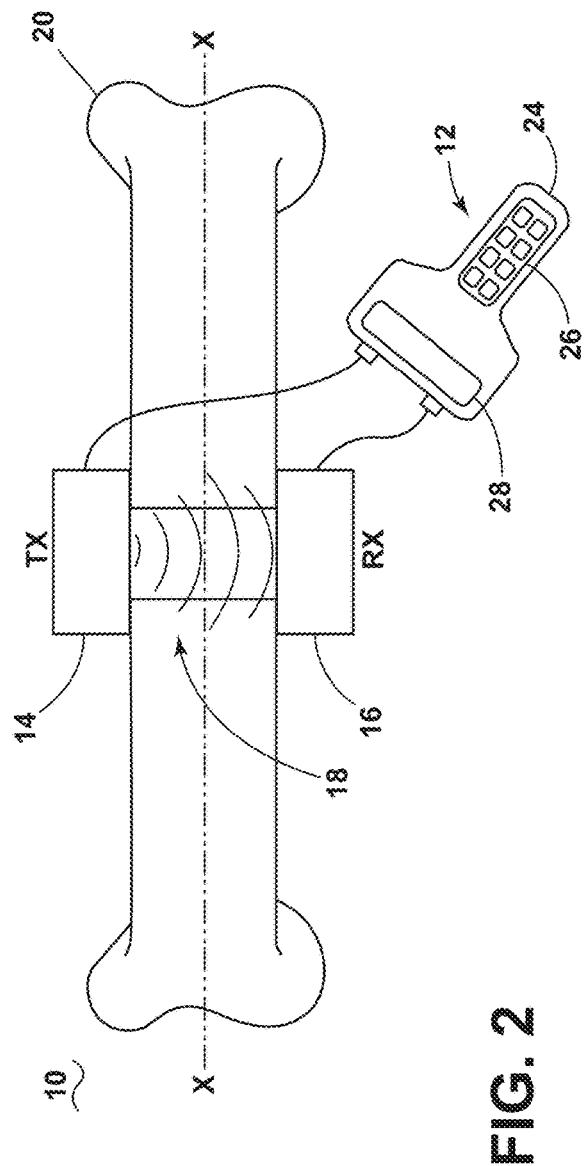
FIG. 2 is a schematic diagram of a system for monitoring osteogenesis using a transmit-receive sensor modality relative to a target site in a bone, including a controller and sensors positioned in a transverse transmission orientation relative to a target site in a bone.

A second transmission orientation is shown in FIG. 2. In FIG. 2, the sensors 14, 16 are provided in a transverse transmission orientation relative to the target site 18 in the bone 20. In transverse transmission, one sensing element, designated in this embodiment as a transmitter (Tx) 14, is positioned on a first side of the target site 18 and another sensing element, designated in this embodiment as a receiver (Rx) 16, is positioned on a second or opposite side of the target site 18 along an axis transverse to the longitudinal axis X of the bone 20. During operation, the transmitter 14 can transmit a wave to the receiver 16 through the bone 20.

For the transmission orientations shown in FIGS. 1-2, the operational mode is defined by the energy source, which is the transmitter 14 that transmits the signal, and by the receiver of the signal, which is the receiver 16 that captures the signal. In both FIGS. 1 and 2, different sensors 14, 16 are shown as acting as transmitters and receivers. This is referred to as a transmit/receive mode (Tx-Rx).

FIG. 1 illustrates the orientation of the two sensors 14, 16 along the longitudinal axis X of the bone 20, such that the transmission path of the signal (left-to-right) is from the distal-to-proximal ends of the target site 18. Alternately, this transmit/receive mode may be reversed, such that the energy is from right-to-left that represents a longitudinal proximal-to-distal energy path. Similarly, FIG. 2 illustrates the orientation of the two sensors 14, 16 transverse to the longitudinal axis X of the bone 20, such that the transmission path of the signal is across the target site 18. Relative to the target site 18, the transmission path may be anterior-to-posterior (AP), medial-to-lateral (ML) or some combination of AP and/or ML, such that the transmission path of the signal is AP, PA, ML, LM, or some combination thereof.

Figure 3:
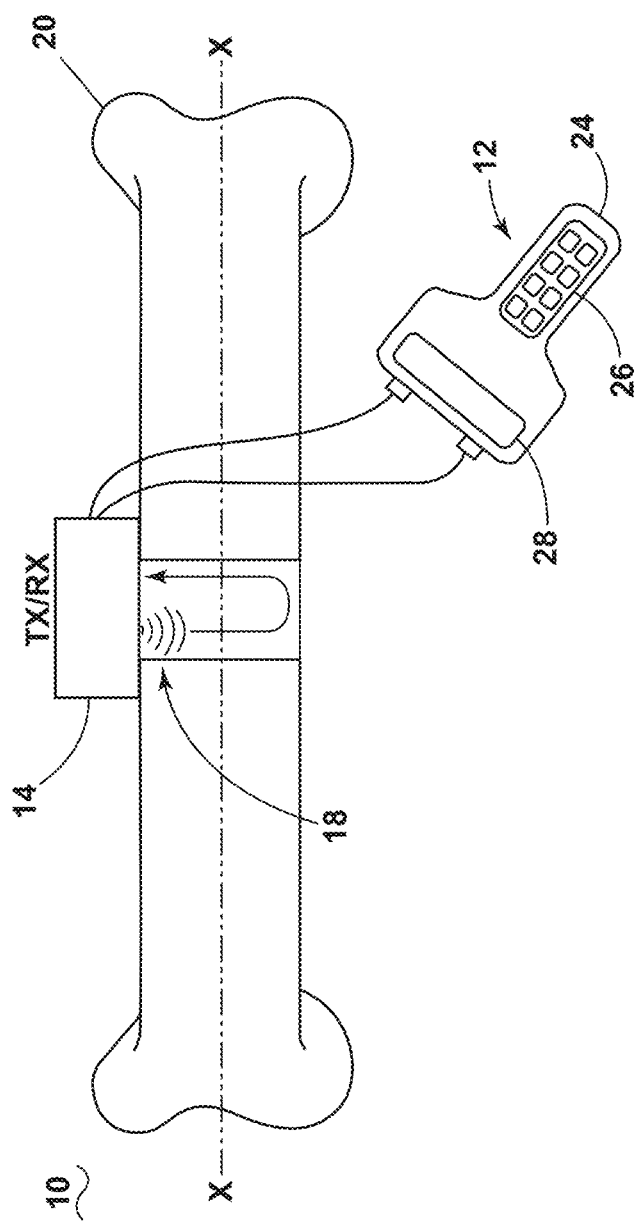
FIG. 3 is a schematic diagram of a system for monitoring osteogenesis using a pulse-echo sensor modality relative to a target site in a bone.

In an alternate mode shown in FIG. 3, one sensor can act as both transmitter and receiver. This is referred to as a pulse-echo mode (PE). The pulse-echo mode employs a single transducer or transceiver 14 as the source of energy and the same transducer or transceiver 14 to capture the signal. It is also contemplated that in some embodiments of the devices, systems and methods disclosed herein, the devices, systems or methods may employ a combination of transmit/receive and pulse-echo modes. Also, while only one sensor pair 14, 16 is shown in the transmit/receive mode of FIGS. 1-2 and only one transceiver 14 is shown in the pulse echo mode of FIG. 3, it is understood that the systems 10 may employ multiple sensor pairs and sensors, respectively.

Regardless of transmission orientation or operational mode, at least one sensor 14, 16 will receive a wave that has propagated through the target site 18 of the bone 20. The controller 12 receives a signal based on the wave and can process the signal or transfer the signal to an external device for processing. For illustration, bone, callus, and other tissues have intrinsic properties, such as but not limited to density and impedance. Certain conditions of the bone will present with different densities; for example, a fracture will have a different density than consolidated bone. Further, different healing stages are also associated with different densities. By measuring the density at the target site 18, bone healing can be quantitatively monitored. It will be understood that in addition to density, the healing state, progression, and trends are affected by fracture/osteotomy geometry, healing symmetry/asymmetry, subsequent wave velocity and attenuation, refraction, reflection, and other interactions with the healing environment that affect the signal patterns and features.

The controller 12 can include a case or housing 24 to hold the components of the controller. In the illustrated example, the controller 12 includes a hand-held device with a user interface having a keypad 26 for inputting information or commands, and a display 28 for showing information to a user of the controller 12. Other configurations of the user interface for the hand-held device are also possible, such as an interface using indicator lights instead or in addition to the display 28. Other configurations of the controller 12 are also possible, such as a single-use throw-away device that is mounted in the cast or fixation system. In other configurations the device may be sterilized, sanitized, and re-usable.

The controller 12 can be a vector processor or array processor where a central processing unit (CPU), FPGA, graphical processing unit (GPU) or the like that implements an instruction set containing instructions that operate on one-dimensional arrays of data called vectors. Patient data can be forwarded to an offsite location which interprets the signals by distributing vector or sensor data. Register masking can be used at the processor to control access to the sensor data at the distributed processor location. Optionally, the distributed or multiprocessor control system can us a sequential program to control operations.

Alternatively to the hand-held device illustrated, the controller 12 can be integrated with a device that is fixed to or worn by the patient, above the fracture or osteotomy, via a cast, air cast, or other fixation device, or via one of the devices shown in FIGS. 11-18. The device can transmit data wirelessly or through a wired connection.

In operation, the sensors 14, 16 are placed on and/or around the target site 18 of the bone 20. The controller 12 is actuated, to send at least one signal, which may be a pulsed signal to the target site 18. A button on the controller 12 can be pressed to initiate the sending of a single signal, or the controller 12 may be automated to send multiple signals. Alternatively, the controller 12 can run automatically, and may not require user input or action. Each signal may include a predetermined pulse frequency and pulse interval, as well as having an overall signal duration. The data can be transmitted to another device so that a physician or other medical practitioner can make a diagnosis. Results can be generated immediately during the test or stored and generated at a later time.

An algorithm can use the data to determine a condition of the bone 20 quantitatively based on the data from the target site 18, including, but not limited to, whether there is a fracture at the target site 18, the healing rate at the target site 18, the healing stage at the target site 18, whether there is osteonecrosis at the target site 18, or whether there is a tumor at the target site 18. The complete algorithm may be stored on-board the controller 12 as described above. Alternatively, the complete algorithm may stored remotely, such as in "the cloud", where only the signal captured is transmitted to a remote device on which the complete algorithm is stored. In yet another example, a modified algorithm (or part of the complete algorithm) can be stored on-board the controller 12, and another modified algorithm (or remaining part of the complete algorithm) can be stored remotely, such as in "the cloud." An initial analysis can be performed by the controller 12, thereby reducing the transmission bandwidth, and the final, more sophisticated analysis can be conducted remotely. In situations where an unacceptable or error signal has been received, the processor can request retransmission from the transmitter for feedback comparison.

It is noted that while FIGS. 1-3 show the systems 10 with the sensors 14, 16 placed on the bone, in at least some embodiments this is for illustration purposes only and that in some embodiments the sensors 14, 16 are external to the patient's body for a system 10 that is applied or mounted on the patient's skin such that the signal transmission is percutaneous. While the device and software will work in a configuration with the sensors placed directly on the bone, the device and software will also advantageously work with the sensors external to the patient's body by transmitting through skin, fat, and muscle through a gap.

Figure 4:
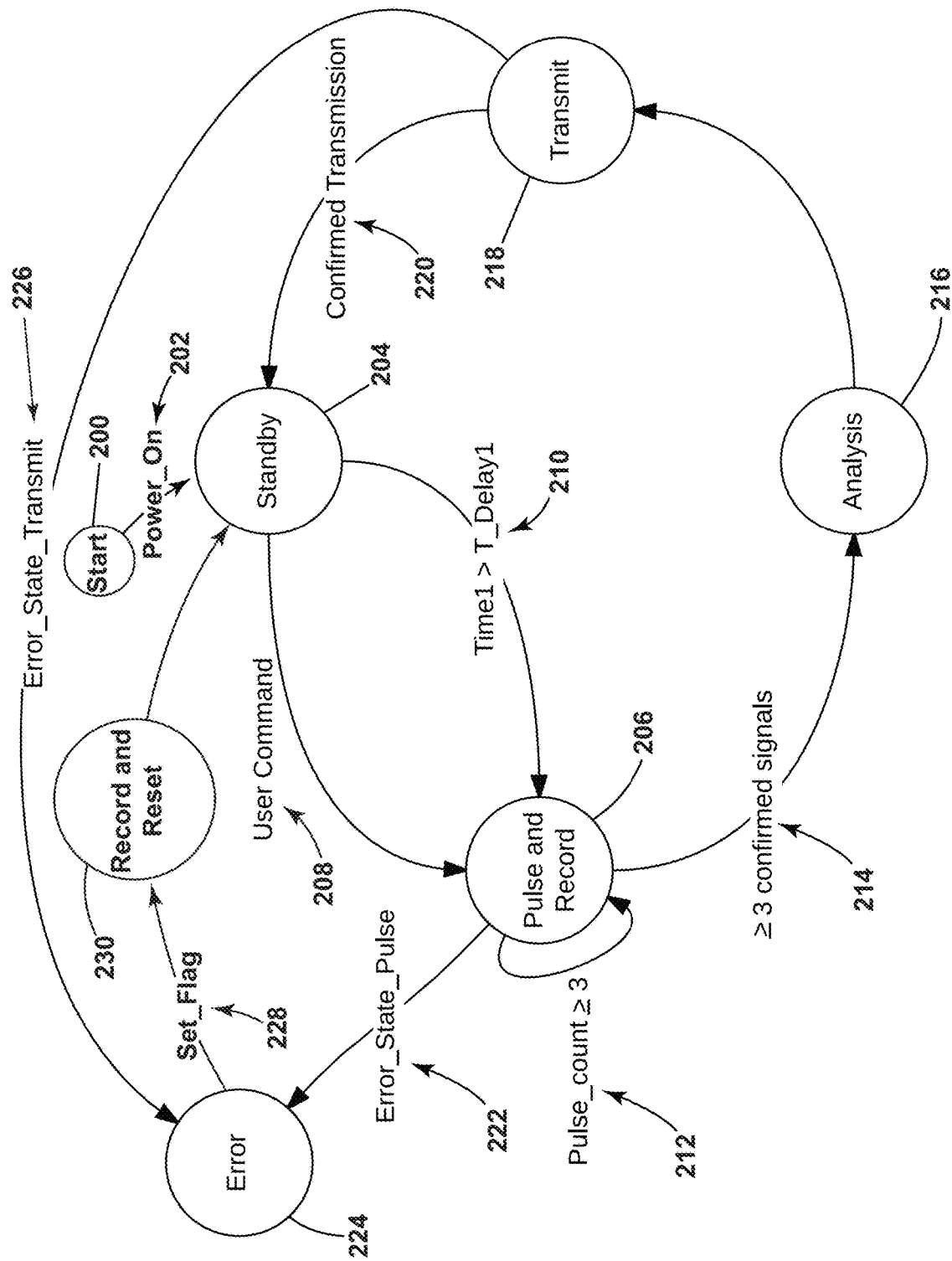
FIG. 4 is a state diagram illustrating one embodiment of the general operation of the system.
Figure 5:
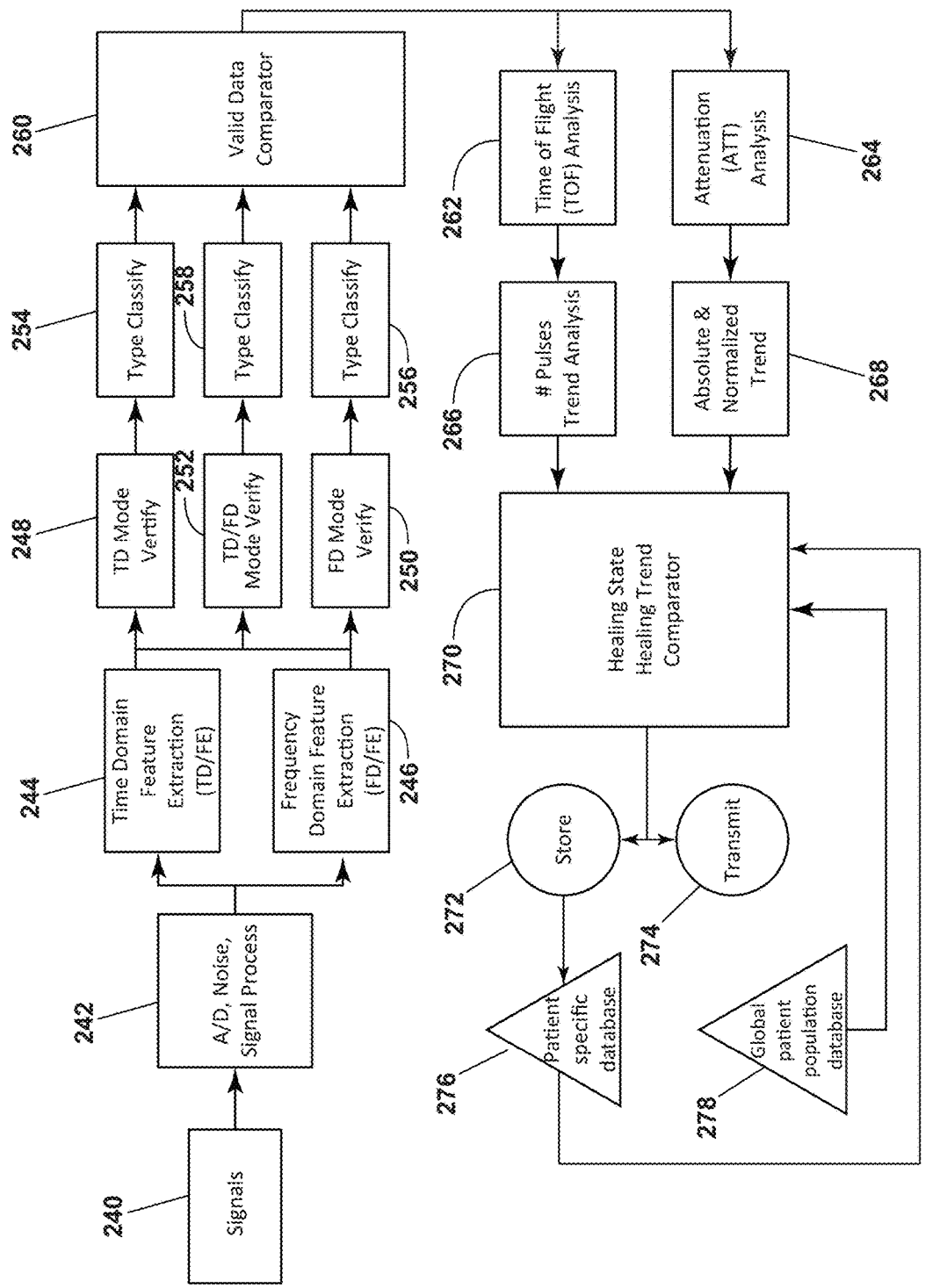
FIG. 5 is a signal analysis flow diagram illustrating one embodiment for the analysis node of FIG. 4.

FIG. 4-5 are diagrams illustrating one embodiment of the general operation of the system and signal analysis. FIG. 4 is a state diagram and includes a node labeled "Analysis," which is further expanded in the signal analysis flow diagram shown in FIG. 5.

In FIG. 4, after starting the device at 200, which can include, among other steps, powering on the device as indicated at 202, the device enters a standby state at 204. To begin capturing data, the device enters a pulse and record state 206. To go from the standby state 204 to the pulse and record state 206, a user may provide a command as indicated at 208, or a timer may exceed a limit as indicated at 210. The command can be entered by pressing a button on the device, such as on the user interface 26, and the timer can be provided in the controller 12. Alternatively, the user command at 208 can be a wireless transmission through a Wi-Fi/Bluetooth or other similar network from a remote location. The use of a timer has the benefit of allowing automatic data collection, analysis, and transmission, while manual operation may offer the user control over when the data collection begins. Automatic initiation of the pulse and record state 206 may be particularly beneficial in scenarios where the device is in a cast or attached to a fixation device. Manual initiation of the pulse and record state 206 may be useful for testing purposes or the medical practitioner may want to gather additional data outside of the normal automatic cycle that uses the timer above. It is noted that embodiments of the device may be operable solely through user command 208, solely through a timer 210, or may be operable in either manner. The user may receive feedback to when the device is placed correctly, relative to the target site.

In the pulse and record state 206, the device can send at least one signal pulse to the target site at 212, and preferably may send multiple pulses of the signal to the target site. In the illustrated example, the device cycles three or more times, i.e. sends three or more pulses to the target site. The pulse frequency, pulse gain, and pulse duration may be varied as well within this condition. The sensor mode and sensor configuration may also be varied within this condition.

Once it has been confirmed that at least one valid signal has been collected at 214, the device transitions to an analysis state at 216. The number of valid signals that need to be collected at 214 will vary depending on the number of pulses cycled at 212. If three or more pulses are sent at 212, three or more valid signals must be confirmed at 214 in order to transition the device to the analysis state 216. The collection of valid signals may also be considered part of the analysis state at 216.

The analysis state 216 is described in more detail with respect to FIG. 5. After analysis of the collected signals is complete, the device transitions to a transmit state at 218, in which data generated by the analysis of the collected signals is transmitted to a data storage device to store the data that is available to a computational engine, which may be within the device (CPU, GPU, etc.), or to the cloud Once it has been confirmed at 220 that the transmission is complete, the device will enter the standby mode 204 again, after which the device may be powered off or may be used again.

An error may occur when the device is in the pulse and record state 206 or the transmit state 218. Some examples of the pulse errors may include, but are not limited to "no signal received", or "received signal power is low", or "sensors misaligned". Some examples of the record errors may include, but are not limited to "memory full", or "corrupted memory", or "stack overflow". Some examples of transmit errors may include, but not be limited to "no WiFi signal", or "parity bit check failed", or "IP address does not exist". If an error occurs during the pulsing of the signal, as indicated at 222, the device can enter an error state 224. If an error occurs during the transmission of the data, as indicated at 226, the device enters the error state 224. In the error state 224, the device may indicate by blinking light sequences, or alternating tones, or by visual display that corrective actions may need to be taken. After a flag is set at 228, the device enters a record and reset state at 230, in which the error is recorded by the device and the device is reset, after which the device will transition to the standby state 204.

FIG. 5 illustrates one embodiment of the analysis state 216 from FIG. 4. At 240, the valid signals are captured as analog signals. The number of valid signals captured may be predetermined or changed by the medical practitioner. In the example from FIG. 4, three or more valid signals are captured. Other parameters that may be altered by the software or by the medical practitioner are the pulse duration, the pulse period, sensor mode, the sensor configuration, and the delays between sample periods.

At 242, analog to digital conversion (A/D), noise cancellation, and other signal pre-processing are performed by the controller 12 as part of a software process or hardware elements. The digital signals are then bundled in data packages for analysis, preferably a number of different analyses. The digital signal data package can include header information such as, but not be limited to, the device settings (mode, frequency, pulse width, etc.), temporal time and date stamps, and bone type, age of the patient, gender of the patient, etc. In some embodiments, at 242, analog to digital conversion (A/D), noise cancellation, and other signal pre-processing may also be performed remotely from the controller 12.

At 244, the digital signal data package undergoes a time domain feature extraction (TD/FE), which identifies and quantifies features in the data such as, but not limited to, the number of peaks, peak magnitudes, peak time of occurrence, valleys, valley magnitudes, valley time of occurrence, peak-valley bundles, number of peak-valley bundles, and bundle envelopes. Further, these features can be normalized and averaged; first order statistics will be calculated.

At 246, the digital signal data package undergoes a frequency domain feature extraction (FD/FE), in which various different frequency domain methods will prepare the data for feature identification and extraction, which include but are not limited to FFT, Yule-Walker, bandpass filters, etc. FD/TE identifies and quantifies features in the data such as, but not limited to, the number of peaks, peak magnitudes, peak-to-peak magnitude deltas, delta-slopes, bandwidth, mean power, frequency at peak, and frequency at mid power.

It may be important to analyze both the time and frequency domains of the data because the healing site is heterogeneous and asymmetric such that the TD or FD analysis alone is not sufficient to determine the signal type.

Next at 248, the sensor mode is verified using the features and other characteristics identified by the TD/FE at 244. The sensor mode is the mode the sensor(s) of the device were in when the signals were collected by the device, and may be pulse-echo (PE) or transmit-receive (TxRx). The sensor mode is also verified at 250 using the features and other characteristics identified by the FD/FE at 246. A third sensor mode verification is done at 252 using the features and other characteristics identified by both the TD/FE at 244 and the FC/FE at 246.

The sensor mode is verified because the subsequent analysis may be different based on the sensor mode. Verifying the sensor mode is a check that provides enhanced patient care so that the healing state and healing trends are accurately diagnosed. In other embodiments, the sensor mode may not be verified, and rather can be identified from header information in the data.

Next, at 254, 256, and 258, the signal type is classified. Signal type is the "shape" of the time domain and frequency domain waveforms (some examples of which are shown in FIGS. 23-29). It considers when the first pulse is observed, the slope of the lines, a wave packet envelope, etc. The type classification is a complex process (i.e. a process having multiple steps) that employs data from the feature extraction in 244 and 246, data from the sensor mode verification in 248, 250, and 252, and data package header information to determine the signal type. The complex process may include several combinations of Bayesian Fusion Analysis, Fuzzy Set Analysis, Neural Networks, etc. The signal type may be a classified based on sensor mode, such as PE vs. TxRX, and a quantified type number, such as, for example, PE Type 1, PE Type 2, PE Type 3, TxRx Type 1, TxRx Type 2, TxRx Type 3, or TxRx Type 4.

TxRx Types 1 and 2 are considered valid data that may be immediately used for feature extraction, trend analysis, healing state determination, and healing rate determination. TxRx Types 3 and 4 are considered invalid data that may indicate misalignment of the sensors, low batteries, or the like. Subsequently, the device diagnostics would execute and corrective actions recommended. PE Type 1 is considered valid data that may be immediately used for feature extraction, trend analysis, healing state determination and healing rate determination. PE Type 2 and 3 are considered invalid data that may indicate misalignment of the sensors, low batteries, or the like. Subsequently, the device diagnostics would execute and corrective actions recommended.

In step 254, for example, the type classification employs the sensor mode verified in 248 and data from the TD/FE in 244, and data package header information to determine the signal type. In step 256, the type classification employs the sensor mode verified in 250 and data from the FD/FE in 246, and data package header information to determine the signal type. In step 258, the type classification employs the sensor mode verified in 252 and data from the TD/FE in 244, data from the FD/FE in 246, and data package header information to determine the signal type.

At 260, a valid data comparator can employ the signal types classified in 254-258 in a complex process that determines which data in the sampling group is valid. The invalid data may be used in determining the Error State in FIG. 4. This could result in simple changes in the positioning of the device or the sensor(s), changing batteries in the device, or require intervention by the medical practitioner. The valid data is used in determining the patient's healing state and healing trends, as described below. The valid and invalid data includes a modified header that adds the findings of 260 with the consensus Mode and Type.

At 262, a time of flight (TOF) analysis is performed to determine the arrival time of the signal pulses at the receiving sensor, which may be the same or a different sensor than the transmitting sensor depending on the sensor mode. At 264, an attenuation (ATT) analysis is performed to determine the degree of signal attenuation between the signal pulses. The TOF analysis and the ATT analysis is used in conjunction with the healing state (HS) and healing trend (HT) stored for the patient to update both. These analyses are conducted on each pulse trial (currently set at 3) and the best of the 3; a consistency check is conducted; and the analyses are conducted for each gain (currently 16 in increments of 3 dB).

At 266, a trend analysis that employs complex processes is performed on the data from the TOF analysis at 262 and the ATT analysis at 264. The TOF and ATT trend analysis are conducted across the 3 trials for each sensor mode, sensor configuration, and sensor frequency. The trend analysis is conducted for each trial gain sweep and for the best signal for each gain. Trend analyses are conducted across the number of sampling periods for that day and across all days. Trend analysis is conducted for the absolute values and for the normalized values.

At 270, a comparator can determine a healing state and a healing trend for the patient using data from the TOF and ATT analysis for the first arriving signal (FAS) and subsequent signals, as well as, features extraction such as but not limited to envelope energy, maximum and minimum within the wave packet, number of peaks, slope of the attenuation profile, wave packet duration, as well as data from a patient specific database 276 and a global patient population database 278. The healing state is also referred to herein at the healing stage, and may be a fracture and inflammatory phase in which a hematoma forms, granulation tissue formation in which a soft callus forms, cartilage callus formation in which a hard callus forms, lamellar bone deposition in which bone forms, and remodeling to the original contour or bone consolidation. The healing trend is the rate of healing and may be/presented as a quantitative scale reflecting x number of days divided by the average number of healing days for that healing state and patient demographics. An example would be HS 1, 7 days of 32 days, for 15-20 year old female otherwise healthy. The healing tread may also be presented in different forms.

It is noted that the healing state and healing trend are dependent upon a number of factors related to the patient, including but not limited to, specific bone being monitored, patient age, patient gender, disease state (smoker, diabetic, etc.), previous healing state, time in previous healing state, time in current healing state, current healing trend, and previous healing trend. So in at least some embodiments, these factors and the results of the trend analysis at 266 and 268 are used to determine the current healing state and healing trend at 270 through complex processes.

At 272, the patient specific data, including but not limited to the healing state and the healing trend, can be stored in a memory on the device/controller 12, or remote from the device. At 274 the patient specific data, including but not limited to the healing state and the healing trend, can be transmitted to the patient, medical practitioner, or to the cloud. In one example, the patient specific data, including but not limited to the healing state and the healing trend, can be transmitted to a remote display to be viewed by a medical practitioner. The medical practitioner can then use the patient specific data to make a diagnosis and/or direct further treatment of the patient.

At 276, a patient specific database can be updated with the patient specific data, including but not limited to the healing state and the healing trend, through a weighting process of population size and other typical actuarial factors. The database may be cloud-based or some subset stored locally to allow faster processing time.

The healing state/healing trend comparator 270 can pull data from the patient specific database 276, as well as a global patient population database 278. The global patient population database 278 may be cloud-based or some subset stored locally to allow faster processing time. The global database can include factors that define the patient demographics, such as but not limited to, gender, age, ethnicity, etc., factors that define the otherwise healthy specific bone material properties such as but not limited to, density, modulus of elasticity, attenuation factor, rigidity, etc., factors that define the life-style choices, such as but not limited to, alcohol consumption, smoker, etc., factors that define the disease state of the patient, such as but not limited to, diabetic, obesity, cancer, etc., factors related to the type of traumatic injury or bone monitoring motivation, such as but not limited to, fracture-type (complete, partial, radial, torsional, etc.), degree of bone loss, surgical procedure (osteotomy, corticotomy, etc.), factors that relate to the geometry of the surgical procedure or the fracture, such as but not limited to, gap width, fixation mode (intramedullary nail, external fixation, cast, etc.), or any combination thereof.

It is noted that the various analysis performed in FIG. 5 may be categorized as deterministic or heuristic. Deterministic processes are classic comparators, such as but not limited to LOGICAL ANDS, ORs, concatenation, parsing, $>$, $<$, etc. Statistical methods may be first order (average, standard deviation, etc.) or higher orders (moments, etc.) Given the same input, a deterministic methods will always yield the same output. Heuristic methods and reasoning engines yield results that are environment-dependent. Fuzzy set methods (FM), neural networks (NN), genetic Algorithms (GE), and combinations thereof are some non-limiting examples of heuristic methods.

In one example, using the device after a break or surgery, from the moment the device is initially turned on the system will start with healing stage 1 (HS1), which is the hematoma. The healing state is stored in memory and updated as the algorithm determines. The global patient population database 278 will have 'normal' healing trend (HT) rates for each stage of healing. The algorithm will compare the actual healing trend of the patient versus that within the global database and transmit this data to the physician. In addition, the system will record in a separate database the healing trend for the patient, thus creating the patient specific database 276. For example, a patient may be found to be healing 10% slower in the first healing stage (HS1). The algorithm may take this into account for the next healing stage (HS2), or the physician may prefer to have the algorithm stick with the global patient population database 278 for the next comparison, or it may combine them in another way for the next comparison.

The signal analysis performed by the algorithm of FIG. 5 may be performed throughout the treatment of a patient with a bone fracture or after surgery. The monitoring regime may include X times per day for Y weeks. In one example, at day X in healing stage 2 (HS2), the following may occur.

A 0.7 MHz signal is collected for PE 1, PE 2, and PE 3 for the medial-medial (MM) configuration at −10 dB through 35 dB (that is, 16 gains in 3 dB increments). This results in 48 signals. A 0.7 MHz signal is collected for TxRx 1, TxRx 2, and TxRx 3 for the ML configuration at −10 dB through 35 dB (again, in 3 dB increments). This results in another 48 different signals. This is repeated for the lateral-lateral (LL), anterior-anterior (AA), posterior-posterior (PP), and anterior-posterior (AP) configurations and for multiple frequencies at each of the MM, ML, LL, AA, PP, and AP configurations. For this example, if 10 frequencies are used, there are 10 (frequencies)×6 (configurations)×48 (signals per position)=2,880 signals. It is noted that while MM is used twice, it is intended to imply a PE mode that may include a single transmitting-receiving sensor or a transmitter and a separate receiver. This applies to all PE modes.

Each signal will be type classified, TOF, ATT, and other analyses will be conducted in the time domain and frequency domain. The features between the signals in this data set are compared and contrasted. In addition, the analysis look at trends from previous data sets from the same healing state in the patient specific database, or an earlier healing state in the patient specific database, or 'normal' data sets from the global patient population database 278.

Using this method, the received signal can be analyzed for type classification by time domain analysis and frequency domain analysis methods that includes but is not limited to absolute comparative first order statistics, Fourier Transform methods, and the like, while extracting and/or referencing the global database and patient specific database for each specific healing state and healing rate that is then used for, but not only, to determine the validity of the data. These are applied to the PE and TxRx modes, and the single and multiple frequencies, and all sensor configurations such as but not limited to AA, PP, AP, MM, LL, ML. Further, the received signal can be analyzed for feature extraction by time domain and frequency domain analysis that includes but is not limited to a sliding window analysis, envelope analysis, and the like, while extracting and/or referencing the global database and patient specific database for each specific healing state and healing rate that is then used for, but not only, to determine the new healing state, new healing rate, error states, reconfiguration states, and the like. These are applied to the PE and TxRx modes, and the single and multiple frequencies, and all sensor configurations such as but not limited to AA, PP, AP, MM, LL, ML. The results or findings from the sliding window analysis, envelope analysis, time domain, frequency domain, Fourier Transform and wavelet methods and the global database and patient specific database are incorporated into a decision analysis method (comparator) that employs heuristic methods such as Fuzzy Set Logic Methods. The results or findings from the sliding window analysis, envelope analysis, time domain, frequency domain, Fourier Transform and wavelet methods and the global database and patient specific database are incorporated into a learning analysis method that employs Neural Networks and Genetic Algorithms.

Figure 6:
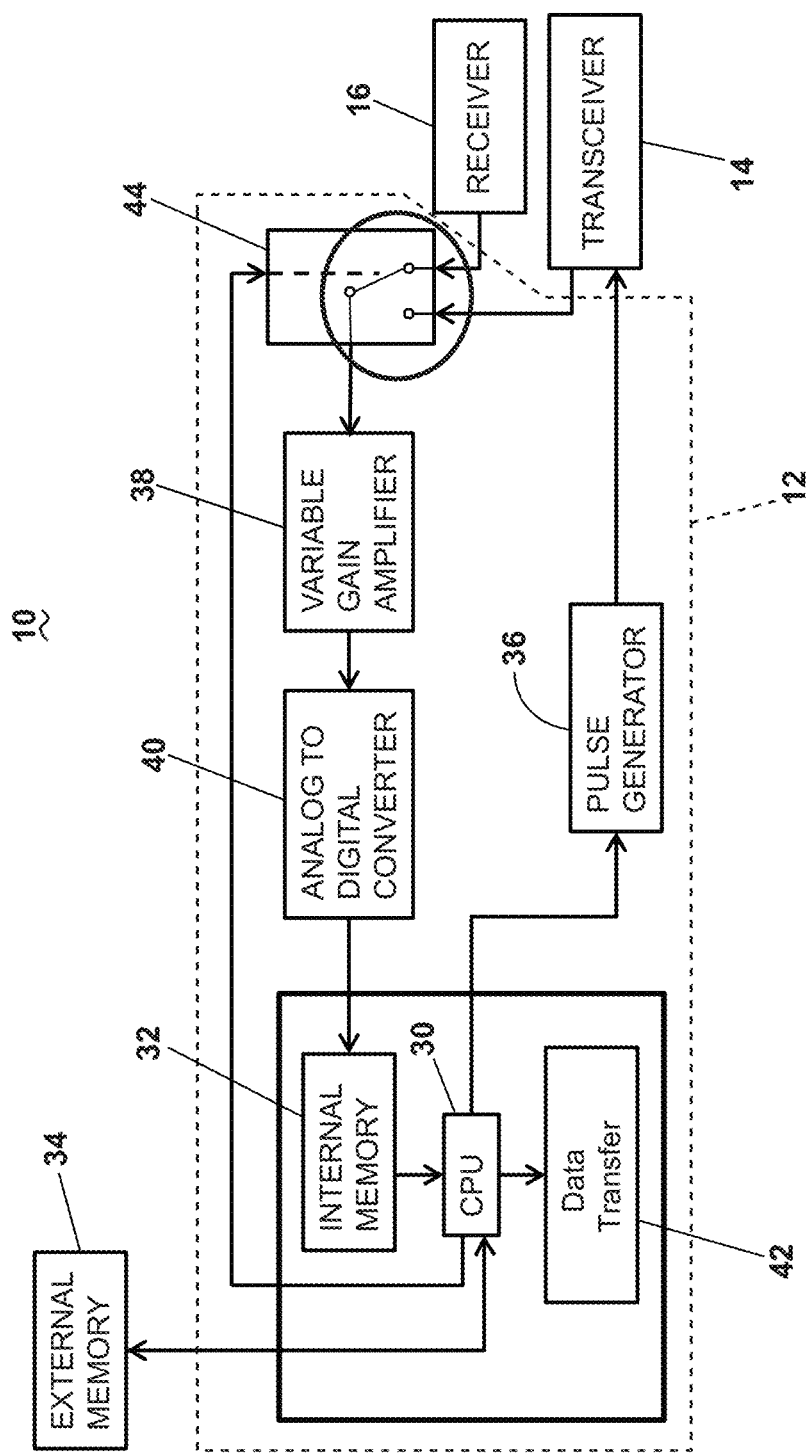
FIG. 6 is a schematic diagram of a system for monitoring osteogenesis operated in a transmit/receive mode.

FIG. 6 is a schematic diagram of one example of the system 10 for monitoring osteogenesis that is operated in a transmit/receive mode. The system includes a central processing unit (CPU) 30 and at least one memory 32, 34. The memory 32, 34 may be used for storing control software that may be executed by the CPU 30 in completing an operation or test with the system. For example, the memory 32, 34 may store one or more pre-programmed test cycles that may be selected by a user and completed by the controller 12. Alternatively, the user can program the test cycle. Both internal and external memory can be provided. In one example, the CPU 30 and internal memory 32 are provided with the controller 12 shown in FIGS. 1-3, and the external memory 34 is provided remote from the controller 12. In one embodiment, the test cycle selection and/or programming can be performed by the physician treating the patient. The system can include compensation routines and systems which function to preadjust transmitter gain levels using techniques such as a pre-chirping or predistortion adjustments.

As discussed above, the controller 12 controls and receives input from one or more sensors. In the illustrated embodiment, a pulse generator 36 is in operable communication with the CPU 30, and is used to drive a sensor in the form of a transceiver 14. The transceiver 14 transmits a wave to a receiver 16 along the longitudinal axis X of the bone 20 (see FIG. 1) or through the bone 20 (see FIG. 2), depending on the orientation of the sensors 14, 16 relative to the bone 20. A signal from the receiver 16 based on the wave is then returned to the controller 12, and can be passed through a variable gain amplifier 38 and an analog-to-digital converter 40 before being stored in the internal memory 32. The signal can be stored in the external memory 34 as well, or alternatively to the internal memory 32.

The controller 12 can pass along the raw signal data for analysis by an external device or can perform analysis or processing of the signal data on board. The controller 12 can further include a data transfer component 42 for sending the raw signal data or the results of the on board analysis to an external device. In one example, the data transfer component 42 is a USB transceiver or a USB dongle, Microdrive, SD card, or holographic memory storage device. The data transfer component 42 may also enable wireless data transmission.

A mode selector can be provided on the controller 12 for selecting the sensor mode (PE or TxRx) of the device. The mode selector can be a switch 44 that selectively couples with either the transceiver 14 or receiver 16 to receive data. The mode selector 44 can be operated by a button or other actuator provided on the controller 12 or can be operated remotely. In the transmit/receive mode shown in FIG. 6, the switch 44 couples with the receiver 16 to receive data from the receiver 16. It is noted that in other embodiments of the system 10, the switch 44 can be eliminated such that the system is only operable in one mode or in both modes.

Figure 7:
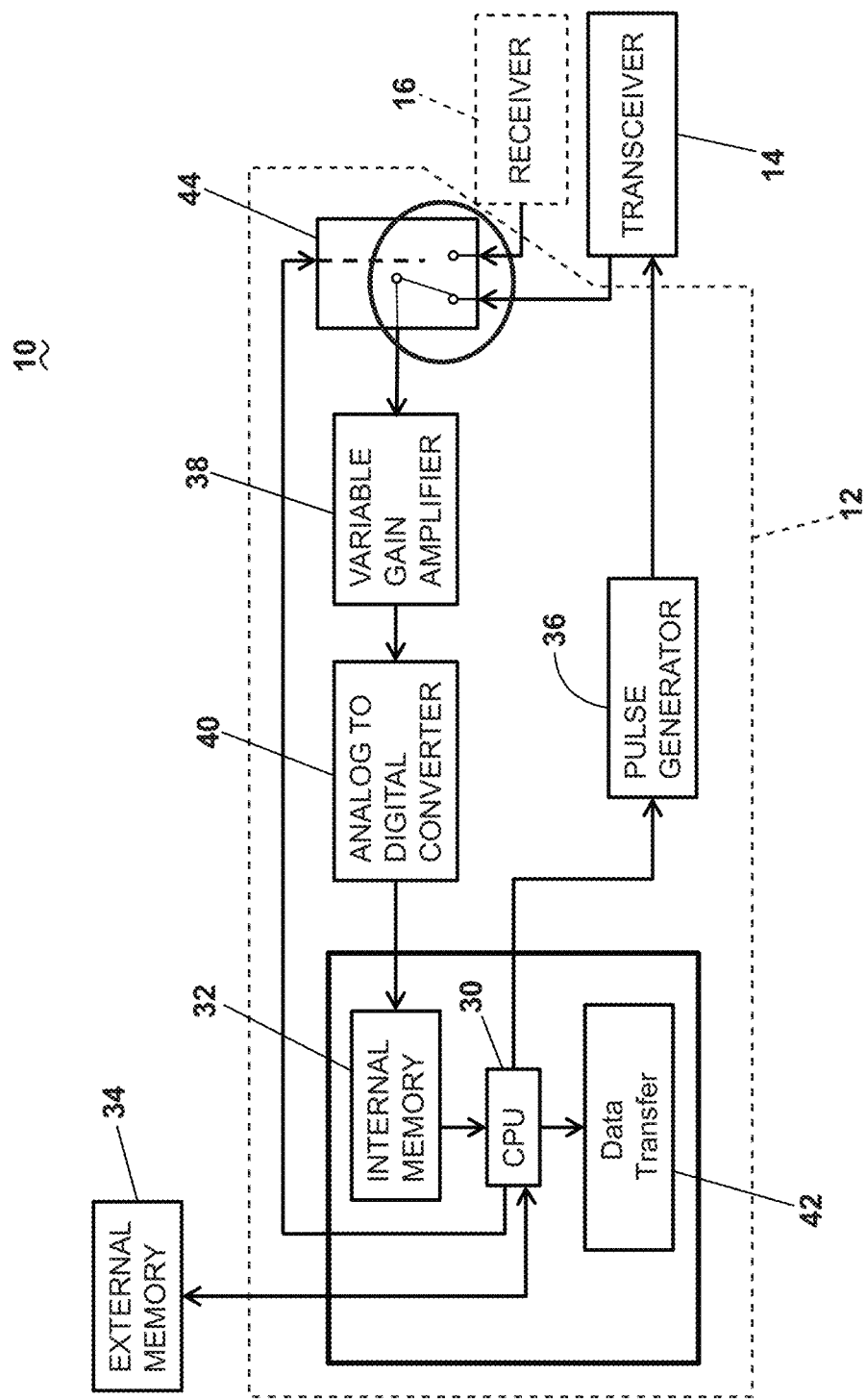
FIG. 7 is a schematic diagram of a system for monitoring osteogenesis operated in a pulse-echo mode.

FIG. 7 is a schematic diagram of one example of the system 10 for monitoring osteogenesis that is operated in a pulse-echo mode. The pulse-echo mode (see FIG. 3) differs from the transmit/receive mode in that the receiver 16 is not required since the transceiver both transmits and receives the wave. The receiver 16 may be eliminated from the system altogether, or as shown in the illustrated embodiment, the controller 12 can control the switch 44 between the transmit/receive mode and the pulse-echo mode. As shown, the switch 44 couples with the transceiver 14 to receive data from the transceiver 14.

Figure 8:
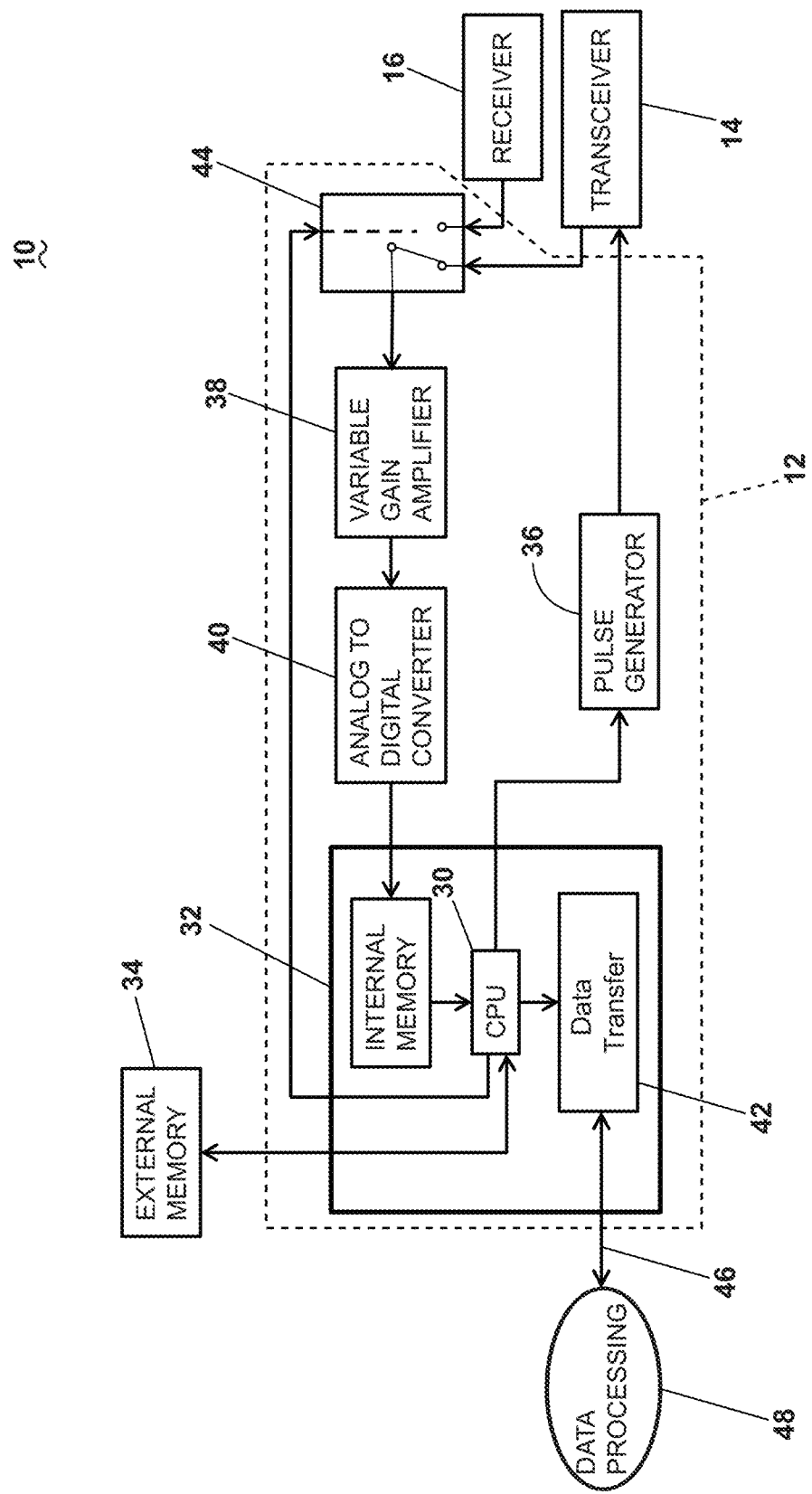
FIG. 8 is a schematic diagram of a system for monitoring osteogenesis with a wired data transfer.

FIG. 8 is a schematic diagram of the system 10 for monitoring osteogenesis where the controller 12 has a wired data transfer. In this embodiment, the controller 12 transfers data via a wired connection 46, such a USB cable or another suitable cable, with the data transfer component 42, which may be a USB transceiver in the case of a USB cable 46. The cable 46 can be temporarily coupled between the controller 12 and an external data processing device 48 to transfer data from the controller 12 to the external device 48 for data processing.

Figure 9:
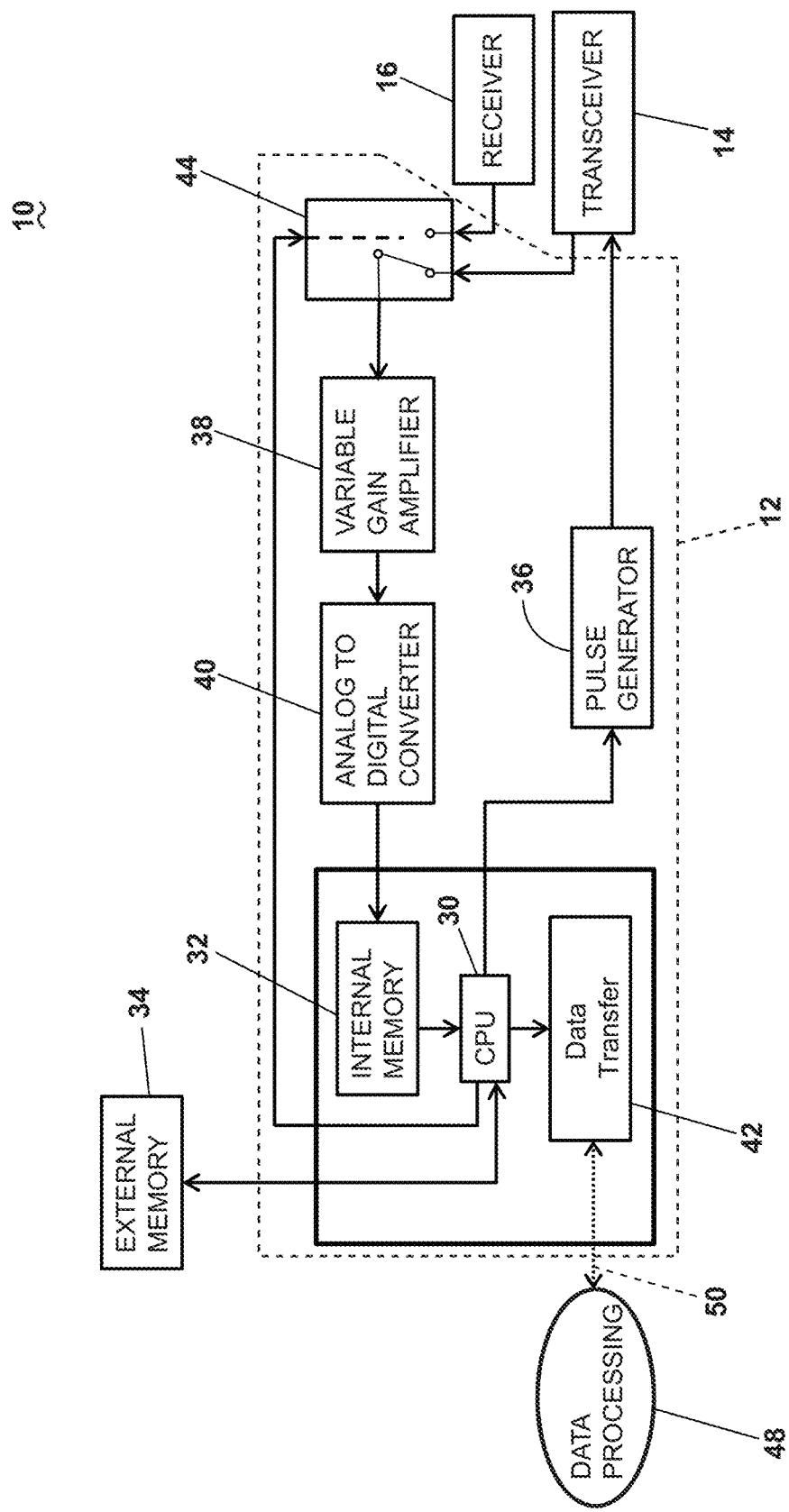
FIG. 9 is a schematic diagram of a system for monitoring osteogenesis with wireless data transfer.

FIG. 9 is a schematic diagram of the system 10 for monitoring osteogenesis where the controller 12 has a wireless data transfer. In this embodiment, the controller 12 transfers data via a wireless connection 50, such Bluetooth®, Bluetooth® Low Energy (LE), ANT™, Zigbee® or other very low- or ultra-low power communication technology, protocol, or the like, with the data transfer component 42. The controller 12 can wirelessly transfer data to the external data processing device 48.

In FIGS. 8-9, the signal analysis is performed by a device other than the controller 12. In this embodiment, the controller 12 transfers the raw signal data for analysis by the external device 48, via a wired or wireless connection 46, 50. The external device 48 analyses or processes the signal data. An algorithm can use the data to determine a condition of the bone quantitatively based on the data taken at the target site, including, but not limited to, whether there is a fracture at the target site, the healing rate at the target site, the healing stage at the target site, whether there is osteonecrosis at the target site, or whether there is a tumor at the target site.

Figure 10:
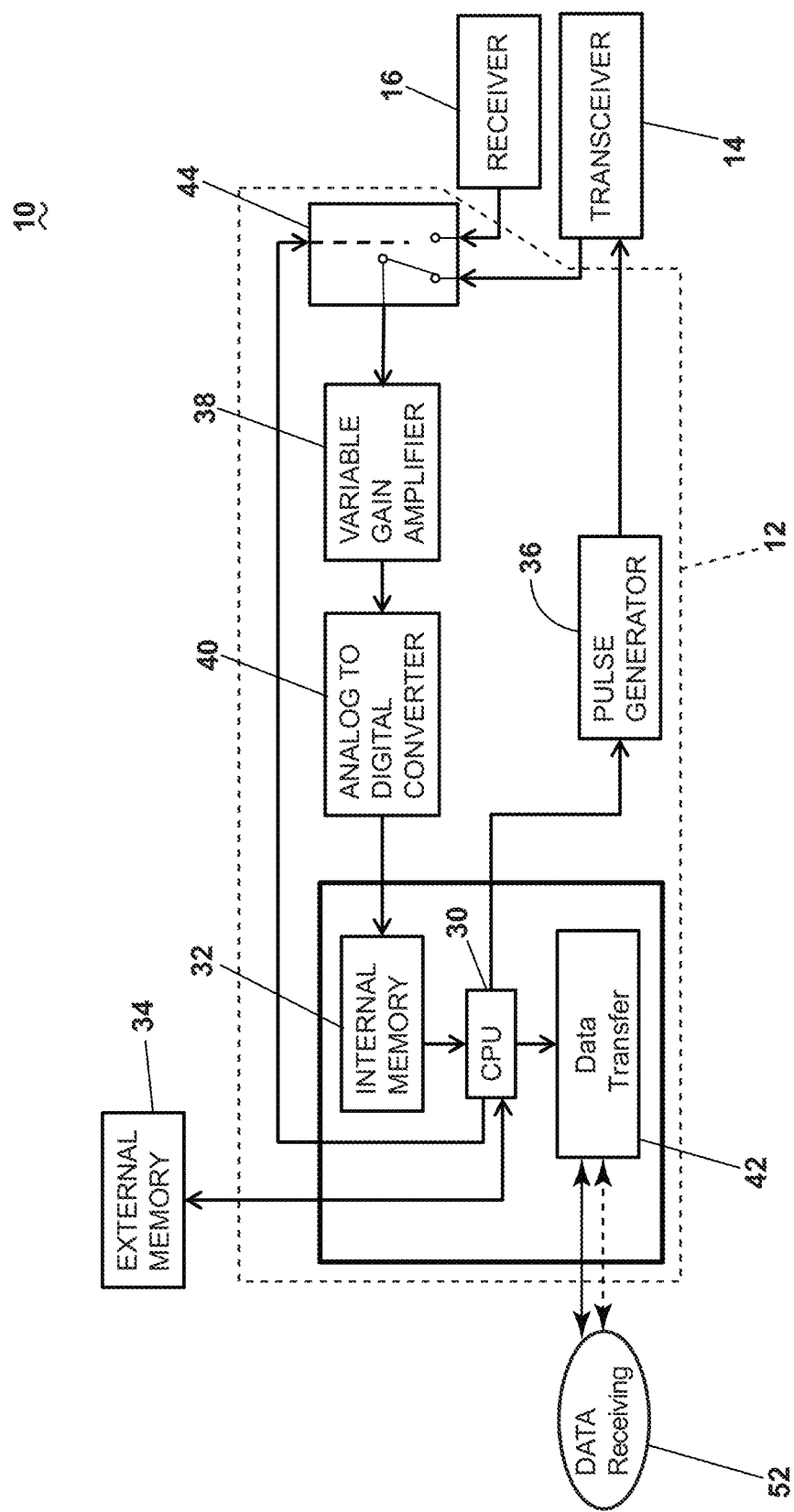
FIG. 10 is a schematic diagram of a system for monitoring osteogenesis with on-board signal analysis.

FIG. 10 is a schematic diagram of the system 10 for monitoring osteogenesis where the controller 12 can perform the signal analysis on board. In this embodiment, the CPU 30 analyses or processes the signal data. An algorithm can use the data to determine a condition of the bone quantitatively based on the data taken at the target site, including, but not limited to, whether there is a fracture at the target site, the healing rate at the target site, the healing stage at the target site, whether there is osteonecrosis at the target site, or whether there is a tumor at the target site. The results of the analysis can be sent to an external data receiving device 52 via a wired or wireless connection, as described for FIGS. 8-9.

It is noted that the system 10 of FIG. 6-10 can be used with sensors placed in either the longitudinal transmission orientation generally described for FIG. 1, or the transverse transmission orientation generally described for FIG. 2, or the pulse echo mode generally described for FIG. 3. Further, the switch 44 allows one system 10 to operate in either the transmit/receive mode or the pulse echo mode.

It is also noted that FIG. 5 is a software that can be resident in the device that is shown in FIGS. 6-10 to analyze the target site of the bone. In another embodiment, the device resident on the patient can be simplified, and may only include sensors, power, pulse generation, and a transmitter. The data analysis can be conducted in the cloud or at a central remote location for all devices, and the results can be transmitted to the physician and/or back to the device. The results can be display on the device using a graphical interface or light indicators. For example, if the target site is found to be healed or fully consolidated, a green light on the display 28 of the device can blink to inform the patient.

Annular Monitoring and/or Stimulation Device

Figure 11:
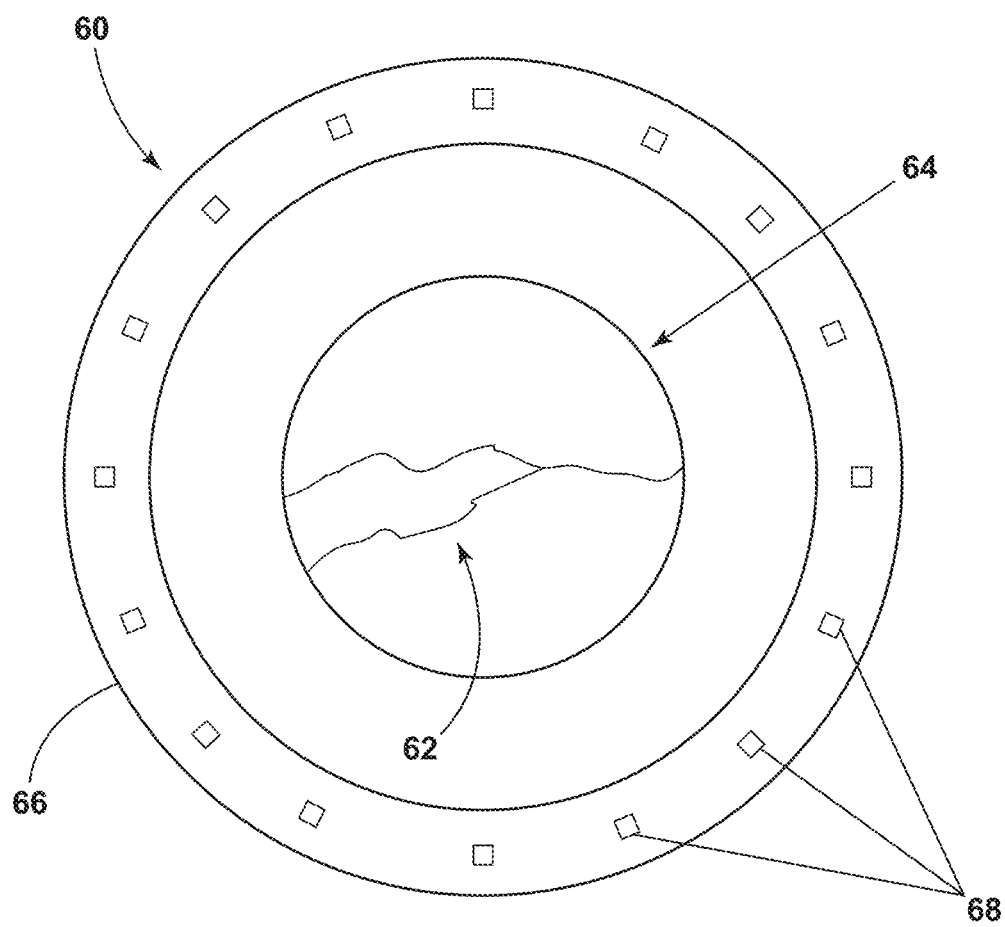
FIG. 11 is a schematic diagram of one embodiment of a bone monitoring and/or stimulation device, illustrating the device positioned around a target site of a bone.

FIG. 11 is a schematic diagram of one embodiment of a bone monitoring and/or stimulation device 60, illustrating the device 60 positioned around a target site 62 of a bone 64.

In FIG. 11, the target site 62 within the bone 64 is shown as having a fracture. As is shown, numerous sensor elements can surround the fracture site. These sensor elements can be transmitters, receivers, or transceivers. While it is envisioned that a single transmitter can be actuated at a time, it is possible to actuate several transmitters simultaneously, either at the same or at different frequencies. Each of these signals can then be received by the plurality of receivers. The signals can then be separated by a processor or processors, such as the CPU 30 or processor(s) of the external data processing device 48 (FIGS. 6-10).

The device 60 includes an annular member 66 carrying a plurality of sensors 68. At least some of the sensors 68 are transmitters capable of transmitting waves, and at least some of the sensors 68 are receivers capable of receiving the transmitted waves and creating a signal representative of a received wave. The annular member 66 is configured to be linked to a controller for transmission of the signal. For example, the annular member 66 may be operably coupled with the controller 12 and/or systems 10 described above with respect to FIGS. 1-10. Some non-limiting examples of suitable sensors 68 for the annular member 66 include, but are not limited to, ultrasound, inductive, capacitive, electromagnetic, magneto-resistive, magneto-restrictive, and piezoelectric sensors, including transceivers or transducers.

The sensors 68 can be spaced at radial intervals around the annular member 66. The radial intervals may be equal or may vary between sensors 68. A single ring of sensors 68 may be provided in the annular member 66; alternatively, multiple rings of sensors 68 may be provided. The annular arrangement of the sensors 68 has an advantage when assessing bone fractures, which do not heal uniformly, because the ring of sensors allows the target site 62 to be assessed from any and all angles, permitting a 360 degree view of the target site 62. One or more of the sensors 68 can be activated as needed to optimally monitor the target site 62. As healing progresses, different sensors 68 can be activated depending on how and where the target site 62 is healing.

Figure 12:
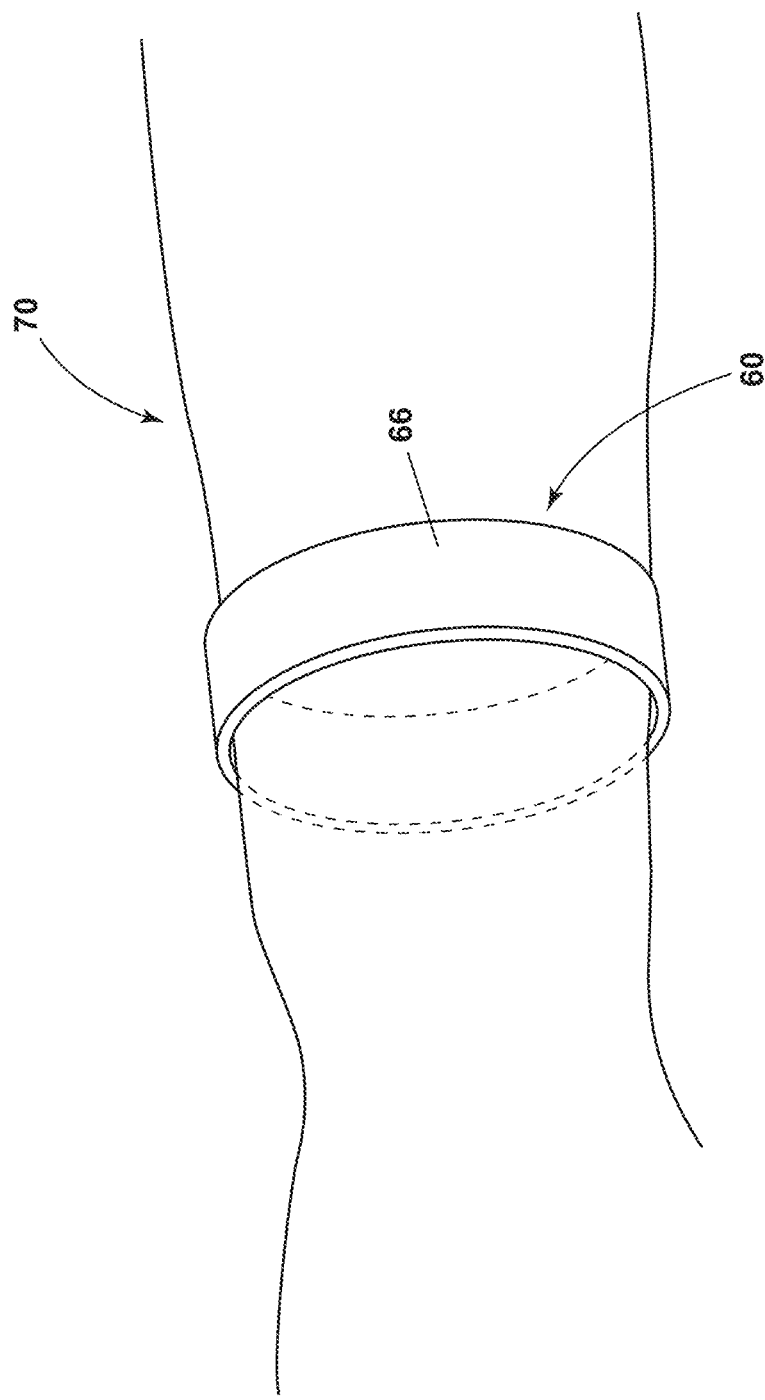
FIG. 12 illustrates the device of FIG. 11 on an arm of a patient.

The annular member 66 is configured to be disposed about the bone 64, as shown in FIG. 11, and is therefore is well-suited for use on the long bones (ex: femur, fibula, tibia, humerus, radius, ulna, metacarpals and metatarsals of the hands and feet, and the phalanges of the fingers and toes). In one embodiment, the annular member 66 can be configured to be placed internally to the patient's body as an implantable or subcutaneous device. In another embodiment, the annular member 66 can placed externally, such as by being provided with or on an external fixator, such as a cast, or worn by the patient. FIG. 12 illustrates one example of the device of FIG. 11 worn on an arm 70 of a patient.

If the annular member 66 is configured to be worn by the patient, as in FIG. 12, the annular member 66 can have a strap-like body made of a fabric, such as a woven fabric webbing material, or molded plastic body, similar to a rubber bracelet. The sensors 68 can be carried externally or internally by the body of the annular member 66. For an annular member 66 configured to be placed internally, the body of the annular member 66 may comprise a biomedically-compatible material.

Figure 13:
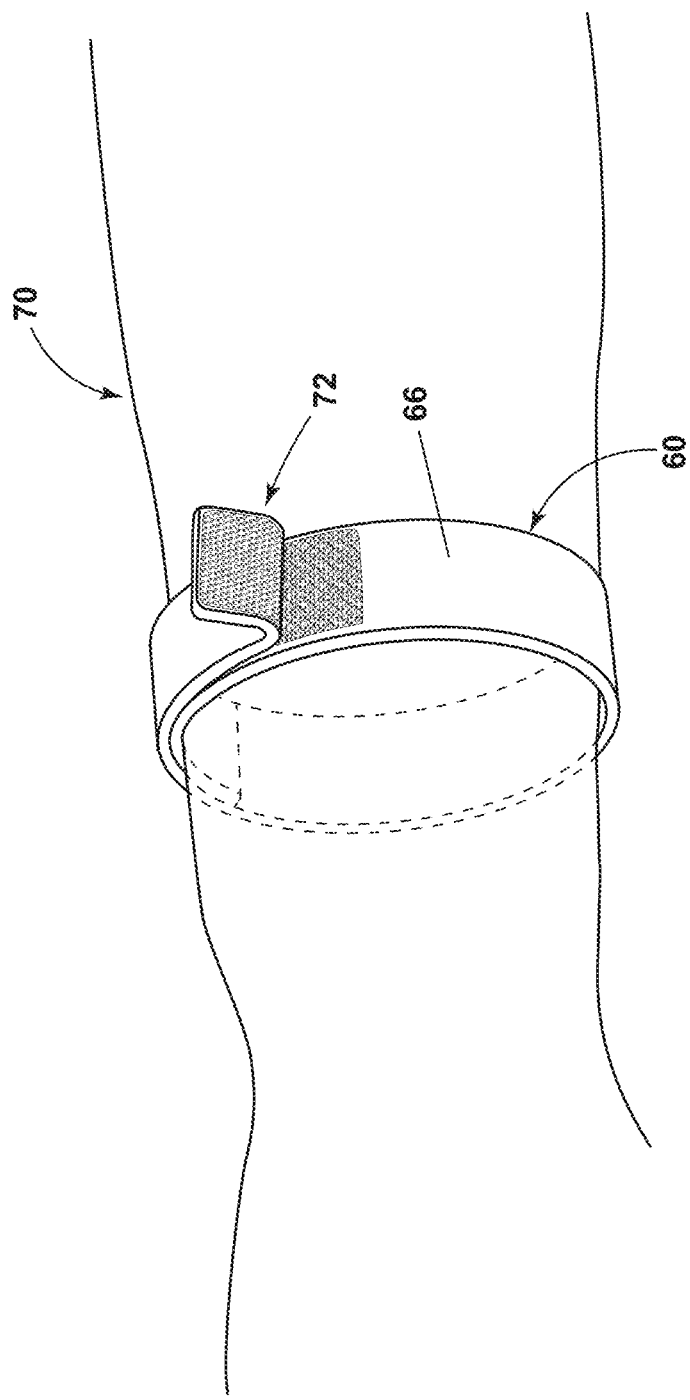
FIG. 13 illustrates the device being removably fixed on the arm of the patient using a hook-and-loop fastener.
Figure 14:
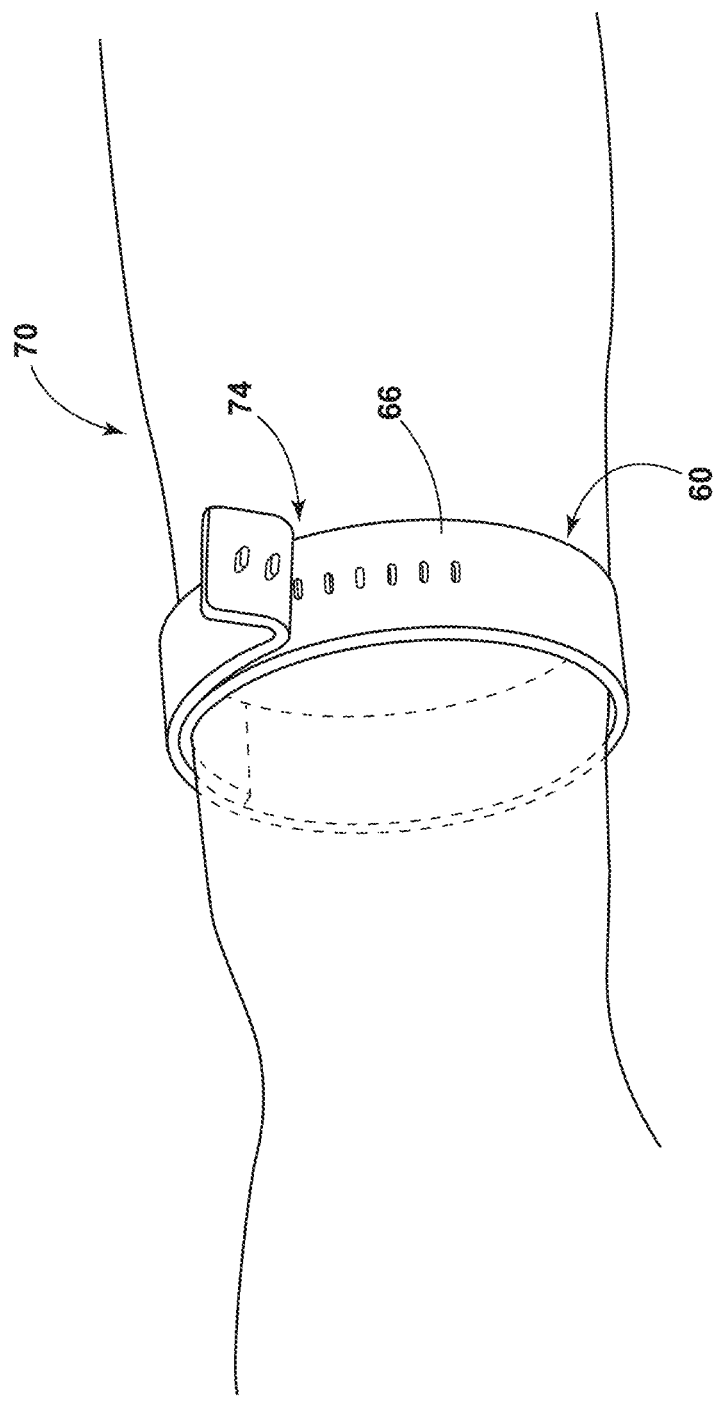
FIG. 14 illustrates the device being removably fixed on the arm of the patient using a tab-and-hole fastener.

Various fasteners can be provided for convenient application and removal of the annular member 66. Two non-limiting examples are illustrated in FIGS. 12-14. FIG. 13 illustrates the device 60 being removably fixed on the arm 70 of the patient using a hook-and-loop fastener 72. FIG. 14 illustrates the device 60 being removably fixed on the arm 70 of the patient using a tab-and-hole fastener 74, similar to certain watchbands. Both of these fasteners 72, 74 allow the annular member 66 to be adjusted within a range of possible sizes to fit different patients and different target sites. The annular member 66 can also take the form of a non-adjustable rubber band bracelet; in this case, multiple sizes can be provided to suit different individuals (ex: adult sizing and child sizing).

The annular member described for FIGS. 11-14 can be used to perform a method of monitoring a bone. With the annular member 66 applied about the arm 70, a wave is transmitted to the bone 64 from at least one sensor 68 which has been designated as a transmitter. The wave is received by at least one sensor 68 which has been designated as a receiver to generate a sensor reading. Data based on the sensor reading is stored, such as by the controller 12, the external memory 34, or one of the external devices 48, 52, as described above with respect to FIGS. 1-10.

Based on the data, a condition of the bone 64 is determined. An algorithm can use the data to determine a condition of the bone 64 quantitatively based on the data taken at the target site 62, including, but not limited to, a physical characteristic such as whether there is a fracture, osteonecrosis, or a tumor at the target site 62, the healing rate at the target site 62, or the healing stage at the target site 62.

Various combinations of sensors 68 can be designated as transmitters and receivers. The designated sensors 68 can be selected to operate the annular device 66 in the pulse-echo mode, the transmit/receive mode, or a combination of both. To operate in the pulse-echo mode, at least one sensor 68 is a transmitter/receiver, or transceiver, capable of both transmitting and receiving waves. In the transmit-receive mode, at least one sensor 68 is designated as transmitter and a different sensor 68 is designated as a receiver. In this instance, the designated transmitter and receiver may be in opposing relationship about the annular member 66. In other instances of the transmit-receive mode, the transmitter and receiver may be various non-opposing relationships about the annular member 66.

Multiple sensors 68 can be designated as transmitters and/or receivers. This can allow the data from the target site 62 to be taken at multiple different locations, and can give a more complete picture of the condition at the entire target site 62.

Using multiple sensors 68 can further allow multiple frequencies of waves to be transmitted to the target site 62, which is desirable because different frequencies affect the signal data, including resolution, attenuation, and penetration. For example, one transmitter can transmit a wave at a first frequency while another transmitter can transmit a wave at a second, different frequency. One frequency can be selected to optimize resolution, but may not penetrate into the bone as far, while another frequency can be selected to optimize penetration, but offers less attenuation. In one example, the first and second frequencies can be in the range of 20 kHz to 200 MHz. More particularly, the first and second frequencies can be in the range of 0.7 MHz-3.0 MHz. In one example, the first frequency can be approximately 1.0 MHz and the second frequency can be approximately 2.25 MHz. These two frequencies may be used together because the 1.0 MHz signal will optimize resolution, but may not penetrate into the bone as far, and the 2.25 MHz signal will optimize penetration, but offers less attenuation.

If multiple sensors 68 are designated as transmitters, the sensors 68 can be actuated sequentially or simultaneously, with the length of wave transmission being overlapping, partially overlapping, or non-overlapping. Whether the data is generated simultaneously or sequentially, the data as a whole can be used and analyzed together to make determinations on the condition of the bone 64.

A pre-existing condition of the bone 64 can be used to determine the number and location of sensors 68 designated as transmitters and receivers. For example, the type of fracture (ex: transverse or oblique, bicortical vs. unicortical) or location of a fracture within a particular bone, such as what type of bone tissue (cortical vs. cancellous) or bone part (ex: epiphysis vs. diaphysis), can be used in designating the transmitter(s) and receiver(s) used for monitoring. The designation of sensors 68 may also be set based on other factors, such as the age of the patient or whether the patient is a smoker.

The annular member 66 described for FIGS. 11-14 can be used to perform a method of osteogenesis stimulation. With the annular member 66 applied about the bone 64, a signal is applied to the target site 62 for stimulation within the bone 64. The signal includes at least one pulse transmitted from at least one of the sensors 68 carried by the annular member 66 and which has been designed as a transmitter. In one example, the signal is an ultrasound or electromagnetic signal. The at least one pulse can comprise a pulse frequency in the range of 0.7 MHz-3.0 MHz. In one example, frequencies of 1.0 MHz and 2.25 MHz can be used. These two frequencies may be used together because the 1.0 MHz signal will optimize resolution, but may not penetrate into the bone as far, and the 2.25 MHz signal will optimize penetration, but offers less attenuation.

Various combinations of sensors 68 can be designated as transmitters. More than one sensor 68 can be designated as a transmitter, and during osteogenesis stimulation, each designated sensor transmitting a wave to the bone 64 from the designated transmitters. The designated transmitters can be actuated sequentially or simultaneously. Using multiple sensors 68 can provide a more complete treatment of the target site 62, as the target site 62 can be stimulated from multiple angles and at multiple frequencies.

A pre-existing condition of the bone 64 can be used to determine the number and location of sensors 68 designated as transmitters. For example, the type of fracture (ex: transverse or oblique, bicortical vs. unicortical) or location of a fracture within a particular bone, such as what type of bone tissue (cortical vs. cancellous) or bone part (ex: epiphysis vs. diaphysis), can be used in designating the transmitter(s) used for stimulation. The designation of sensors 68 may also be set based on other fractures, such as the age of the patient or whether the patient is a smoker.

The signal can be applied according to a treatment protocol requiring a certain number of applications within a given time frame. For example, the signal can be applied X times daily for Y weeks. Concurrently with osteogenesis stimulation, a condition of the bone 64 at the target site 62 can be monitored, and X and Y may be determined using information from the monitoring method described above. The results of the monitoring can be used to determine the number and location of sensors 68 designated as transmitters for the osteogenesis stimulation method, or at least one pulse frequency and pulse interval for the signal used for stimulation. For example, the type or location of a fracture, the healing stage, or a healing rate of a fracture can be used in designing the treatment scheme. Thus, the treatment scheme can be personalized for the patient.

FIG. 15 is an illustration of another embodiment of a bone monitoring and/or stimulation device 80. The device 80 may be substantially similar to the annular device 60 described above with respect to FIGS. 11-14, but may include an annular member in the form of a cuff or sleeve 82 carrying a plurality of sensors 84 spaced around the sleeve 82 as well as along the sleeve 82. The annular sleeve 82 can be used to perform the methods of monitoring a bone and osteogenesis stimulation described above for the annular member 60. Fractures occur in a wide variety of configurations, typically asymmetrically. Using a multitude of sensors 84 in a sleeve 82 placed around the fracture and/or osteotomy provides for bone monitoring and/or stimulating asymmetrical fracture and/or osteotomies as well as symmetrical fracture and/or osteotomies.

As with the annular embodiment described above, at least some of the sensors 84 are transmitters capable of transmitting waves, and at least some of the sensors 84 are receivers capable of receiving the transmitted waves and creating a signal representative of a received wave. The sleeve 82 is configured to be linked to a controller for transmission of the signal. For example, the sleeve 82 may be operably coupled with the controller 12 described above with respect to FIGS. 1-10. Some non-limiting examples of suitable sensors 84 for the annular sleeve 82 include, but are not limited to, ultrasound, inductive, capacitive, electromagnetic, magneto-resistive, magneto-restrictive, and piezoelectric sensors, including transceivers or transducers.

The sensors 84 can be spaced at radial intervals around the sleeve 82. The radial intervals may be equal or may vary between sensors 84. The sensors 84 are also spaced along the sleeve 82. In the illustrated embodiment, multiple rings 86 of sensors 84 are arranged on the sleeve 82. The multiple ring arrangement of the sensors 84 has an advantage when assessing bone fractures, which do not heal uniformly, because the ring 86 of sensors 84 allows the fracture to be assessed from any and all angles and along the length of the bone. One or more of the sensors 84 can be activated as needed to optimally monitor the fracture. As healing progresses, different sensors 84 can be activated depending on how and where the fracture is healing. Further, with sensors 84 extending along the length of the sleeve 82, fractures extending generally along the longitudinal axis of the bone may be addressed.

The sleeve 82 is configured to be disposed about a bone, and is therefore is well-suited for use on the long bones (ex: femur, fibula, tibia, humerus, radius, ulna, metacarpals and metatarsals of the hands and feet, and the phalanges of the fingers and toes). In one embodiment, the sleeve 82 can be configured to be placed internally to the patient's body. For a sleeve 82 configured to be placed internally, the sleeve 82 may comprise a biomedically-compatible material. In another embodiment, the annular sleeve 82 can placed externally, such as by being provided with or on an external fixator, or worn by the patient.

FIG. 16 illustrates the sleeve 82 of FIG. 15 worn on an arm 88 of a patient. If the sleeve 82 is configured to be worn by the patient, as in FIG. 16, the sleeve 82 can have a strap-like body made of a fabric, such as a woven fabric webbing material, or molded plastic body. The sensors 84 can be carried externally or internally by the body of the sleeve 82. Various fasteners can be provided for convenient application and removal of the sleeve 82, such as the hook-and-loop fastener 72 or tab-and-hole fastener 74 shown in FIGS. 13-14. Both of these fasteners 72, 74 allow the sleeve 82 to be adjusted within a range of possible sizes to fit different patients and different target sites.

Hand-Held Monitoring and/or Stimulation Device

Figure 17:
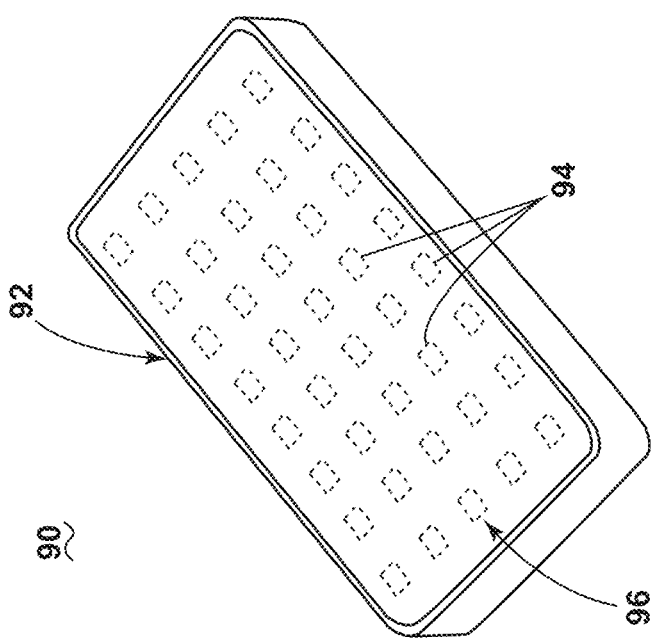
FIG. 17 is an illustration of another embodiment of a bone monitoring and/or stimulation device.

FIG. 17 is an illustration of another embodiment of a bone monitoring and/or stimulation device 90. The device 90 may be similar to the annular devices 60, 70 described above with respect to FIGS. 11-16, but may include a hand-held member 92 carrying an array of sensors 94. At least some of the sensors 94 are transmitters capable of transmitting waves, and at least some of the sensors 94 are receivers capable of receiving the transmitted waves and creating a signal representative of a received wave. The hand-held member 92 is configured to be linked to a controller for transmission of the signal. For example, the hand-held member 92 may be operably coupled with the controller 12 described above with respect to FIGS. 1-10. Fractures occur in a wide variety of configurations, typically asymmetrically. Using a multitude of sensors 94 in a hand-held member 92 placed over the fracture and/or osteotomy provides for bone monitoring and/or stimulating asymmetrical fracture and/or osteotomies as well as symmetrical fracture and/or osteotomies. Some non-limiting examples of suitable sensors 94 for the annular member include, but are not limited to, ultrasound, inductive, capacitive, electromagnetic, magneto-resistive, magneto-restrictive, and piezoelectric sensors, including transceivers or transducers.

The hand-held member 92 can include a relatively flat body, and a grid of sensors 94 can be spaced over the body. In the illustrated example, the sensors 94 are arranged in an array 96 of multiple rows and columns. Other sensor arrangements are possible. The sensor array 96 has an advantage when assessing bone fractures, which do not heal uniformly, one or more of the sensors 94 can be activated as needed to optimally monitor and/or stimulate the fracture. As healing progresses, different sensors 94 can be activated depending on how and where the fracture is healing.

Figure 18:
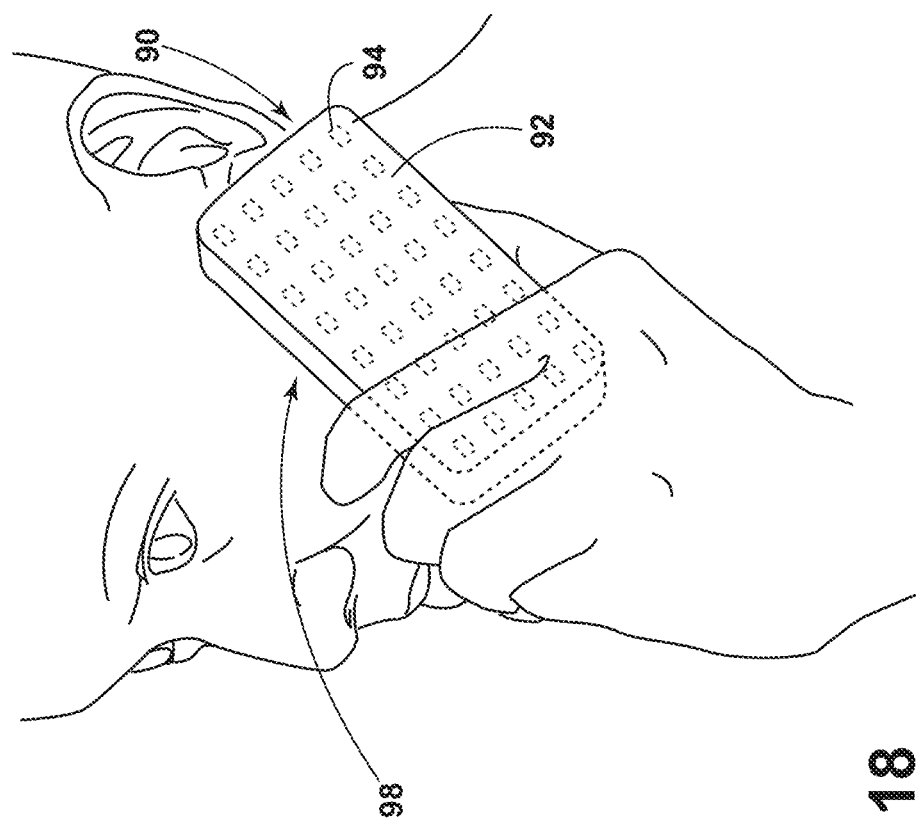
FIG. 18 illustrates the device of FIG. 17 held against the jaw of a patient.

The hand-held member 92 is configured to be held against a body part. The hand-held member 92 may is well-suited for use on bones with an irregular shape, or which are otherwise located so as to be unconducive to a wearable device, such as the clavicle, mandible, or other craniomaxillofacial bones. For example, FIG. 18 illustrates the device 90 of FIG. 17 held against the jaw 98 of a patient for monitoring or treating the mandible. In another embodiment, the device 90 can be a hands-free device adapted to be worn by the patient.

In one embodiment, the hand-held member 92 may conveniently be integrated with a personal communications device, such as a smartphone. Data can be transferred directly between the smartphone and a medical practitioner. The smartphone can be provided with an app for interfacing with the monitoring and/or stimulating processes.

The hand-held member 92 described for FIGS. 17-18 can be used to perform a method of monitoring and/or stimulating a bone. With the device 90 placed against the body, generally adjacent a target site in a bone, a wave is transmitted to the bone from at least one sensor 94 which has been designated as a transmitter. The wave is received by at least one sensor 94 which has been designated as a receiver to generate a sensor reading. Data based on the sensor reading is stored, such as by the controller 12, the external memory 34, or one of the external devices 48, 52, as described above with respect to FIGS. 1-10.

Based on the data, a condition of the bone, here the jaw 98, is determined. An algorithm can use the data to determine a condition of the bone quantitatively based on the data taken at the target site, including, but not limited to, a physical characteristic such as whether there is a fracture, osteonecrosis, or a tumor at the target site, the healing rate at the target site, or the healing stage at the target site.

Various combinations of sensors 94 can be designated as transmitters and receivers. The designated sensors 94 can be selected to operate the hand-held member 92 in in the pulse-echo mode, the transmit/receive mode, or a combination of both. To operate in the pulse-echo mode, at least one sensor 94 is a transmitter/receiver, or transceiver, capable of both transmitting and receiving waves. In the transmit-receive mode, at least one sensor 94 is designated as transmitter and a different sensor 94 is designated as a receiver.

Multiple sensors 94 can be designated as transmitters and/or receivers. This can allow the data from the target site to be taken at multiple different locations, and can give a more complete picture of the condition at the entire target site.

Using multiple sensors 94 can further allow multiple frequencies of waves to be transmitted to the target site, which is desirable because different frequencies affect the signal data, including resolution, attenuation, and penetration. For example, one transmitter can transmit a wave at a first frequency while another transmitter can transmit a wave at a second, different frequency. One frequency can be selected to optimize resolution, but may not penetrate into the bone as far, while another frequency can be selected to optimize penetration, but offers less attenuation. In one example, the first frequency can be approximately 1.0 MHz and the second frequency can be approximately 2.25 MHz. These two frequencies may be used together because the 2.25 MHz signal will optimize resolution, but may not penetrate into the bone as far, and the 1.0 MHz signal will optimize penetration, but offers less attenuation.

If multiple sensors 94 are designated as transmitters, the sensors 94 can be actuated sequentially or simultaneously, with the length of wave transmission being overlapping, partially overlapping, or non-overlapping. Whether the data is generated simultaneously or sequentially, the data as a whole can be used and analyzed together to make determinations on the condition of the bone.

A pre-existing condition of the bone can be used to determine the number and location of sensors 94 designated as transmitters and receivers. For example, the type of fracture (ex: transverse or oblique, bicortical vs. unicortical) or location of a fracture within a particular bone, such as what type of bone tissue (cortical vs. cancellous) or bone part (ex: epiphysis vs. diaphysis), can be used in designating the transmitter(s) and receiver(s) used for monitoring. The designation of sensors 94 may also be set based on other fractures, such as the age of the patient or whether the patient is a smoker.

The hand-held member described for FIGS. 17-18 can also be used to perform a method of osteogenesis stimulation of a target site of a bone, similar to the method of osteogenesis stimulation described above for the annular device 60.

Multi-Frequency Monitoring

The various devices and systems described for FIGS. 1-18 can be used to perform a method of monitoring a bone, described below. Other devices and systems can also be used to perform the following method. A flow chart generally depicting one embodiment of the method 100 is shown in FIG. 19. The sequence of steps discussed for FIG. 19 is for illustrative purposes only and is not meant to limit the method 100 in any way as it is understood that the steps may proceed in a different logical order, additional or intervening steps may be included, described steps may occur simultaneously, or described steps may be divided into multiple steps, without detracting from the invention.

The method 100 can include transmitting a wave having a first frequency from a first sensor positioned adjacent to the bone at 102 and transmitting a wave having a second frequency, different from the first frequency, from a sensor positioned adjacent to the bone at 104. The waves having the first and second frequencies are received, such as by the same or a different sensor, to generate sensor readings at 106.

The first and second frequencies can be in a range of 0.7 MHz-3.0 MHz. In one example, the signal applied is an ultrasound or electromagnetic signal.

Data based on the sensor readings is stored at 108, such as by the controller or an external device, as described above with respect to FIGS. 1-10. Based on the data, a condition of the bone is determined at 110. An algorithm can use the data to determine a condition of the bone quantitatively based on the data taken at the target site, including, but not limited to, a physical characteristic such as whether there is a fracture, osteonecrosis, or a tumor at the target site, the healing rate at the target site, or the healing stage at the target site.

Multiple sensors can be designated as transmitters and/or receivers in steps 102 and 104. This allows multiple frequencies of waves to be transmitted to the target site, which is desirable because different frequencies affect the signal data, including resolution, attenuation, and penetration.

For example, one transmitter can transmit a wave at a first frequency at 102 while another transmitter can transmit a wave at a second, different frequency at 104. One frequency can be selected to optimize resolution, but may not penetrate into the bone as far, while another frequency can be selected to optimize penetration, but offers less attenuation. In one example, the first frequency can be approximately 1.0 MHz and the second frequency can be approximately 2.25 MHz.

The frequencies may also be set based on a pre-existing condition of the bone. For example, the type of fracture (ex: transverse or oblique, bicortical vs. unicortical) or location of a fracture within a particular bone, such as what type of bone tissue (cortical vs. cancellous) or bone part (ex: epiphysis vs. diaphysis), can be used in determining the frequencies used for monitoring. The frequencies may also be set based on other fractures, such as the age of the patient or whether the patient is a smoker.

If multiple sensors are designated as transmitters, the sensors can be actuated sequentially or simultaneously, with the length of wave transmission being overlapping, partially overlapping, or non-overlapping. Whether the data is generated simultaneously or sequentially, the data as a whole can be used and analyzed together to make determinations on the condition of the bone.

For this method, the sensors can be positioned internal or external to the body, including, but not limited to, being carried by the annular device or hand-held device described for FIGS. 11-18. Examples of the sensors include, but are not limited to, ultrasound, inductive, capacitive, electromagnetic, magneto-resistive, magneto-restrictive, and piezoelectric sensors, including transceivers or transducers.

The method 100 can operate with sensors in a longitudinal transmission orientation or in a transverse transmission orientation, and with sensors operating in the pulse-echo mode, the transmit/receive mode, or a combination of both. To operate in the pulse-echo mode, the first sensor, second sensor, or both the first and second sensors, is a transmitter/receiver, or transceiver, capable of both transmitting and receiving waves. In the transmit-receive mode, the first sensor, second sensor, or both the first and second sensors, are transmitters, and the waves are received by one or more corresponding receivers positioned adjusting the bone. Separate receivers can be provided for the first and second sensors, or one of the sensors can act as a receiver for the waves transmitted by the other, and vice versa.

Monitoring of the condition using method 100 may be repeated or ongoing, such that the frequencies used for monitoring can periodically be updated. For example, different frequencies may provide optimal data based on the healing stage of the target site. As healing processes, different frequencies can be used depending on how and where the fracture is healing.

The method 100 can, for example, be used to monitoring fracture in a bone, and is quantified by determining a healing rate or a healing stage of the fracture at 110. In another example, the method 100 can be used in combination with other medical treatment in order to guide the treatment, one such example being osteogenesis stimulation. In another example, the method 100 can be used for monitoring a bone tumor, and is quantified by determining whether the tumor is benign or cancerous at 110.

Method of Bone Stimulation

The various devices and systems described for FIGS. 1-18 can be used to perform a method of stimulating osteogenesis in a bone at a predetermined site, as described below. Other devices and systems can also be used to perform the following method. A flow chart generally depicting one embodiment of the method 120 is shown in FIG. 20. The sequence of steps discussed for FIG. 20 is for illustrative purposes only and is not meant to limit the method 120 in any way as it is understood that the steps may proceed in a different logical order, additional or intervening steps may be included, described steps may occur simultaneously, or described steps may be divided into multiple steps, without detracting from the invention.

The method 120 can include the steps of monitoring a condition in the bone at the site at 122, determining at least one pulse frequency and at least one pulse interval for stimulating osteogenesis in the bone based on the monitored condition at 124, and applying a signal to the site at 126, where the signal includes multiple pulses having the at least one pulse frequency and provided at the least one pulse interval.

Performing monitoring in conjunction with stimulation allows a medical professional to develop a treatment scheme that is tailored to the individual and to the condition of the bone itself. The monitored condition at 122 may be a physical characteristic such as whether there is a fracture, osteonecrosis, or a tumor at the target site, the healing rate at the target site, or the healing stage at the target site.

In one implementation, various combinations of pulse frequencies and pulse intervals can be used for stimulation at 126. The pulse frequency and pulse interval used for stimulation can be determined by a condition of the bone. In one example, the signal applied is an ultrasound or electromagnetic signal. The at least one pulse frequency can be in the range of 0.7 MHz-3.0 MHz. The stimulation method can further include determining at least one treatment time duration based on the monitored condition. The signal can be applied for the determined time duration.

Multiple pulse frequencies and/or pulse intervals can be determined at 124 based on the monitored condition. For example, at least two different pulse frequencies can be selected, and at least one pulse at each pulse frequency can be applied to the site for stimulation. Additionally, at least two different pulse intervals can be selected, and at least one signal using each pulse interval can be applied to the site for stimulation at 126.

Monitoring of the condition at 122 may be repeated or ongoing, such that the pulse frequencies and pulse intervals used for stimulation at 126 can periodically be updated. For example, different frequencies or intervals may provide optimal stimulation based on the healing stage of the target site. Using multiple frequencies and variable intervals optimizes the treatment to stimulate bone healing, and may shorten the overall time required for treatment.

The signal can be applied at 126 according to a treatment scheme requiring a certain number of applications within a given time frame. For example, the signal can be applied X times daily for Y weeks, where X and Y may be determined using information from the monitoring method described above. Thus, the treatment scheme can be personalized for the patient.

The method 120 can, for example, be used to stimulate the healing of a fracture in a bone. In this case, it can be helpful to also quantify the healing rate or a healing stage of the fracture at 122. The quantified healing rate and/or healing stage can then be used to determine or modify the pulse frequencies and pulse intervals at 124 used for future stimulation treatments. The treatment scheme is therefore developed based on quantitative data, rather than qualitative data like average healing times or X-rays. This method 120 can reduce the overall time required for treatment, as it can speed bone healing and consolidation.

In addition to the various devices and systems described for FIGS. 1-18, the stimulation method 120 can also be performed using other devices. In one example, the device that applies that signal can be a mouthpiece that the user, in this case the patient, bites onto for an orthodontic treatment. The mouthpiece includes multiple sensors, and can be mounted on a bodypiece that the user holds or hangs out of the mouth. One example of a configuration is the AcceleDent Aura by OrthoAccel Technologies, Inc. In another embodiment, only a mouthpiece is provided for a hands-free option.

In another embodiment, the method 120 can include the steps of monitoring a condition in the bone at the site as set forth with respect to FIG. 19 in conjunction with stimulating osteogenesis in the bone. Osteogenesis can be stimulated by applying a signal to the site having a fixed pulse frequency and interval. In one example, the stimulation device can deliver ultrasound pulsed at 20% (1:4) and at 1000 Hz (1 kHz)—therefore, there are 1000 cycles per second, and each cycle is thus $\frac{1}{1000}$ of a second (i.e. a millisecond). In that millisecond, there will be 20% ultrasound and 80% not ultrasound. The ultrasound 'on' cycle will therefore be 0.2 milliseconds (200 microseconds or 200 µs) followed by a 'gap' of 0.8 milliseconds (or 800 µs). This pulse frequency and pulse interval are FDA approved for the non-invasive treatment of non-unions. The signal can be applied for 20 minutes per day for the duration of treatment. One example of a suitable device for applying stimulation is the Exogen Ultrasound Bone Healing System. Other pulse frequencies, pulse intervals, and treatment times can be used to stimulate osteogenesis, in conjunction with monitoring.

Method of Identifying and Diagnosing Bone Tumors

The various devices and systems described for FIGS. 1-18 can be used to perform a method of identifying and diagnosing a tumor in a bone at a predetermined site, described below. Other devices and systems can also be used to perform the following method. A flow chart generally depicting one embodiment of the method 140 is shown in FIG. 21. The sequence of steps discussed for FIG. 21 is for illustrative purposes only and is not meant to limit the method 140 in any way as it is understood that the steps may proceed in a different logical order, additional or intervening steps may be included, described steps may occur simultaneously, or described steps may be divided into multiple steps, without detracting from the invention.

Tumors have different densities than bone, and cancerous tumors also have different densities than benign tumors. Using the various systems/devices described above, a density measurement can be taken at a target site of a bone and used determine if a tumor is present, and to further diagnose the type of tumor present. Other measurements may be taken in addition to or alternatively to a density measurement. Density is one of several intrinsic properties that affect the behavior of the signal, which can be characterized and used to diagnose tumor. It will be understood that in addition to density, the healing state, progression, and trends are affected by tumor geometry, symmetry/asymmetry, subsequent wave velocity and attenuation, refraction, reflection, and other interactions with the environment that affect the signal patterns and features.

The method 140 can include transmitting a wave having a first frequency from a first sensor positioned adjacent to the bone to the site at 142 and transmitting a wave having a second frequency, different from the first frequency, from a sensor positioned adjacent to the bone to the site at 144. The waves having the first and second frequencies are received, such as by the same or a different sensor, to generate sensor readings at 146.

Data based on the sensor readings is stored at 148, such as by the controller or an external device, as described above with respect to FIGS. 1-10. Based on the data, a determination is made as to whether a tumor is present at the site a 150. If a tumor is determined to be present, it can further be determined whether tumor is malignant or benign at 150. An algorithm may use the data to make the diagnosis, may provide data for a clinician to make the diagnosis.

Method of Use with X-Ray

Figure 22:
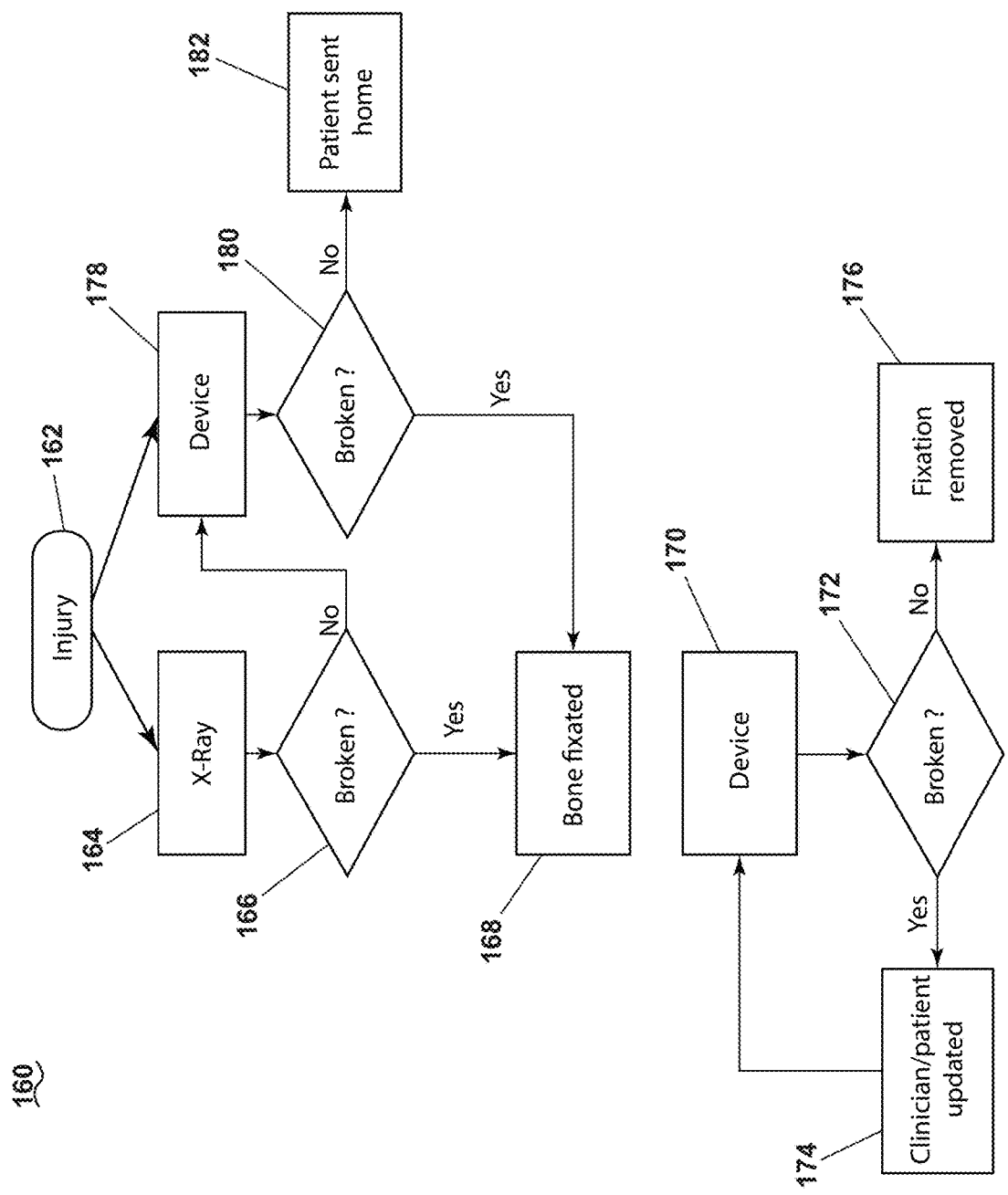
FIG. 22 is a flow chart illustrating a method of diagnosing a fracture a bone in conjunction with X-ray.
Figure 23:
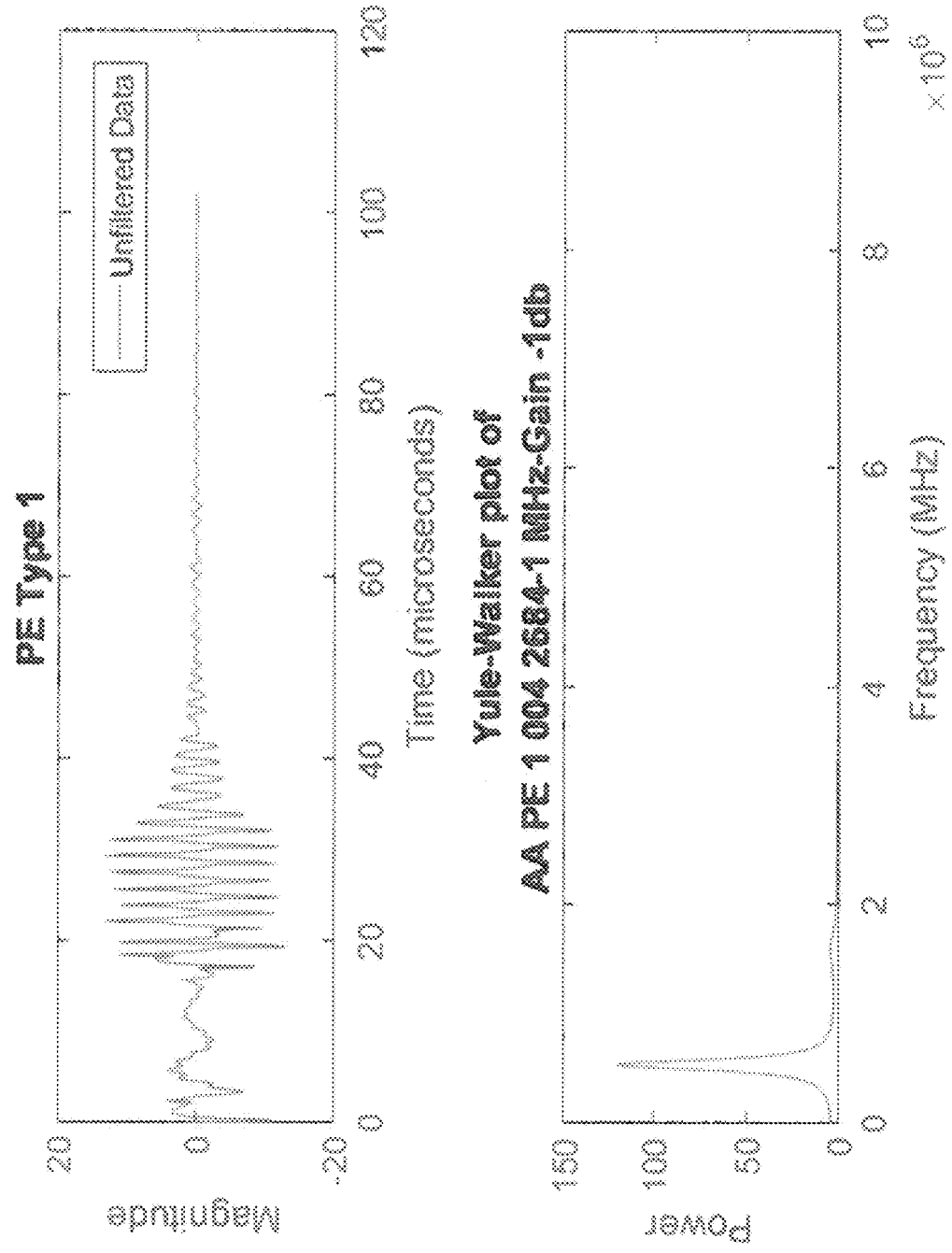
FIG. 23 is an example of a time domain and a frequency domain waveform for a PE Type 1 signal.
Figure 24:
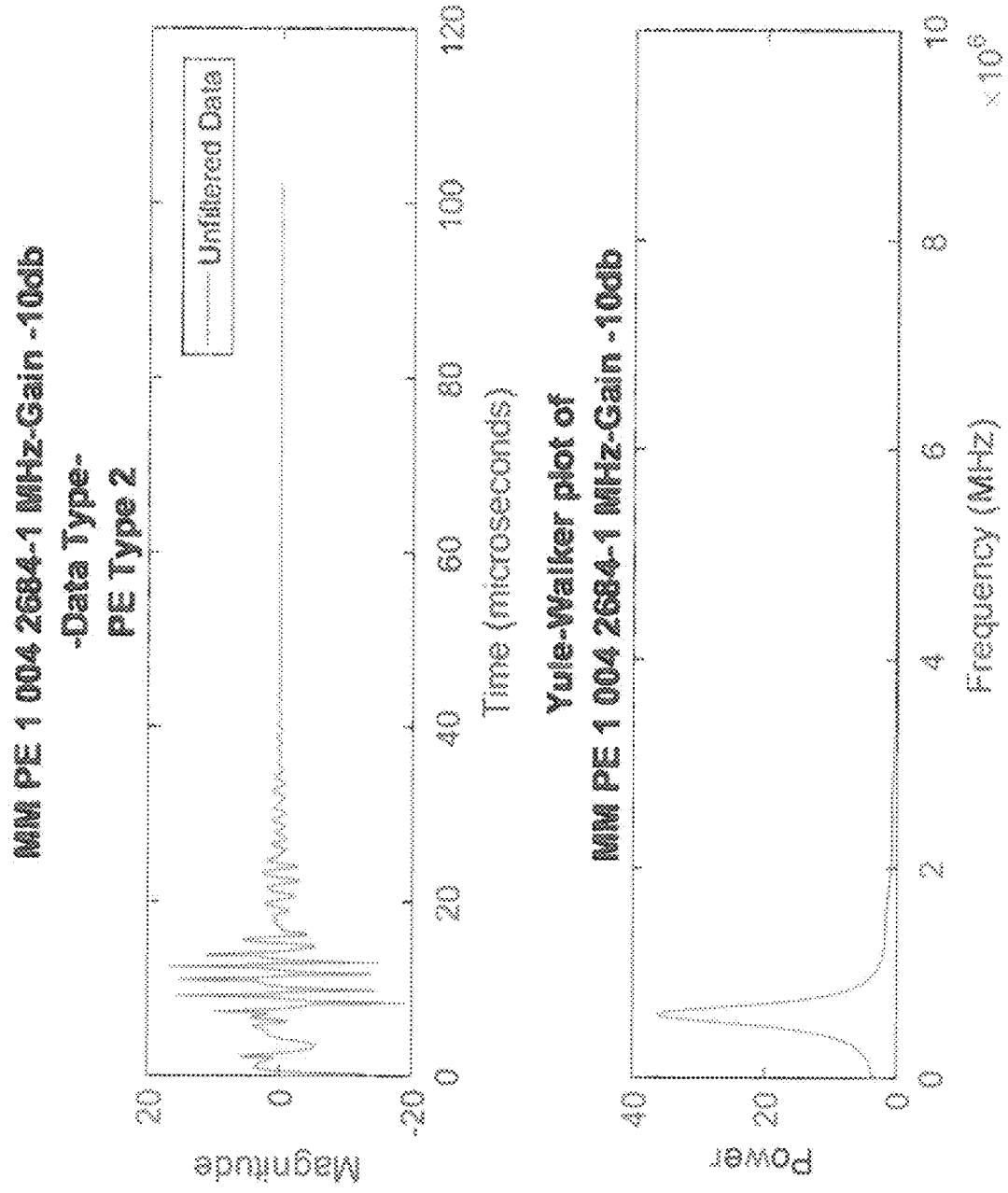
FIG. 24 is an example of a time domain and a frequency domain waveform for a PE Type 2 signal.
Figure 25:
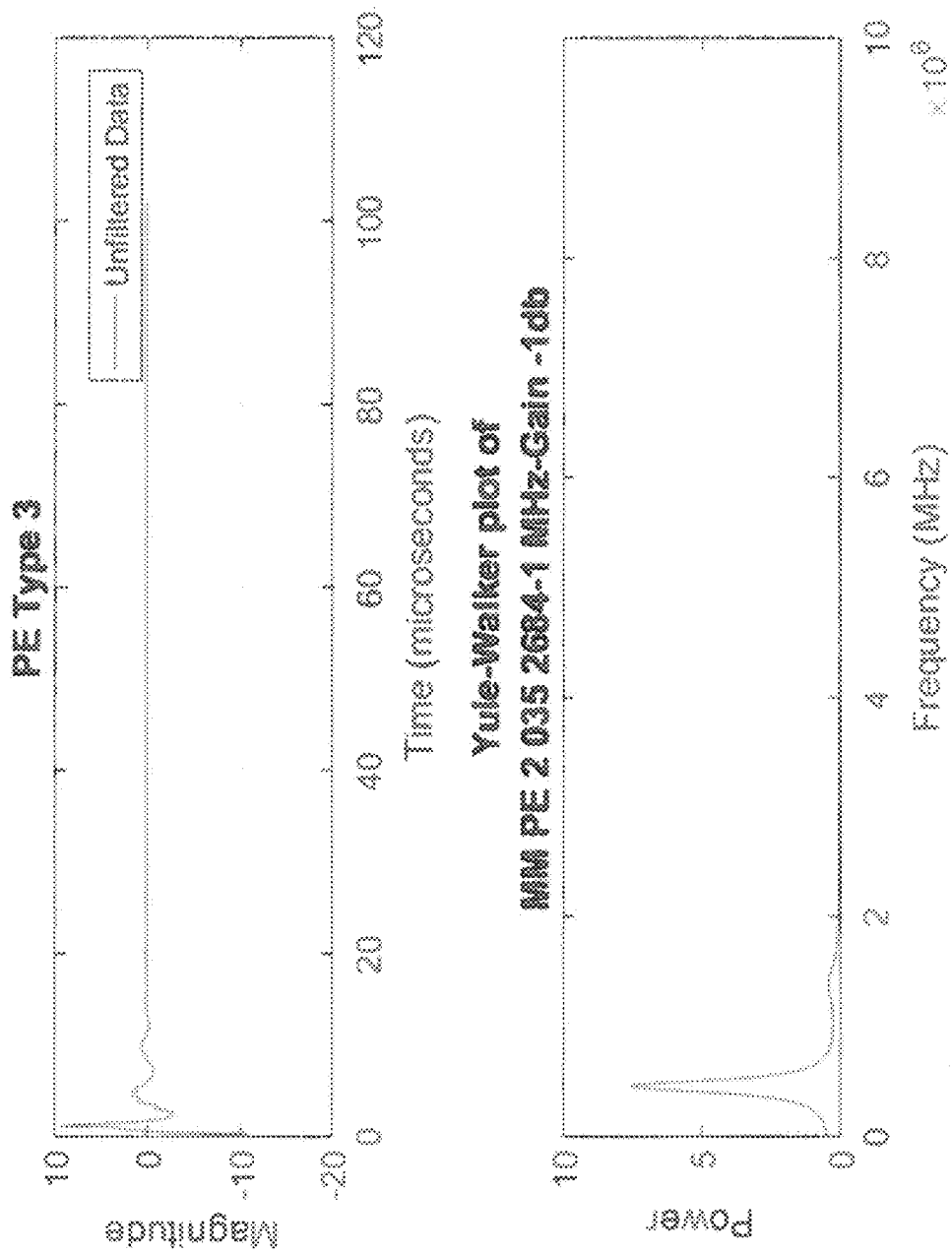
FIG. 25 is an example of a time domain and a frequency domain waveform for a PE Type 3 signal.
Figure 26:
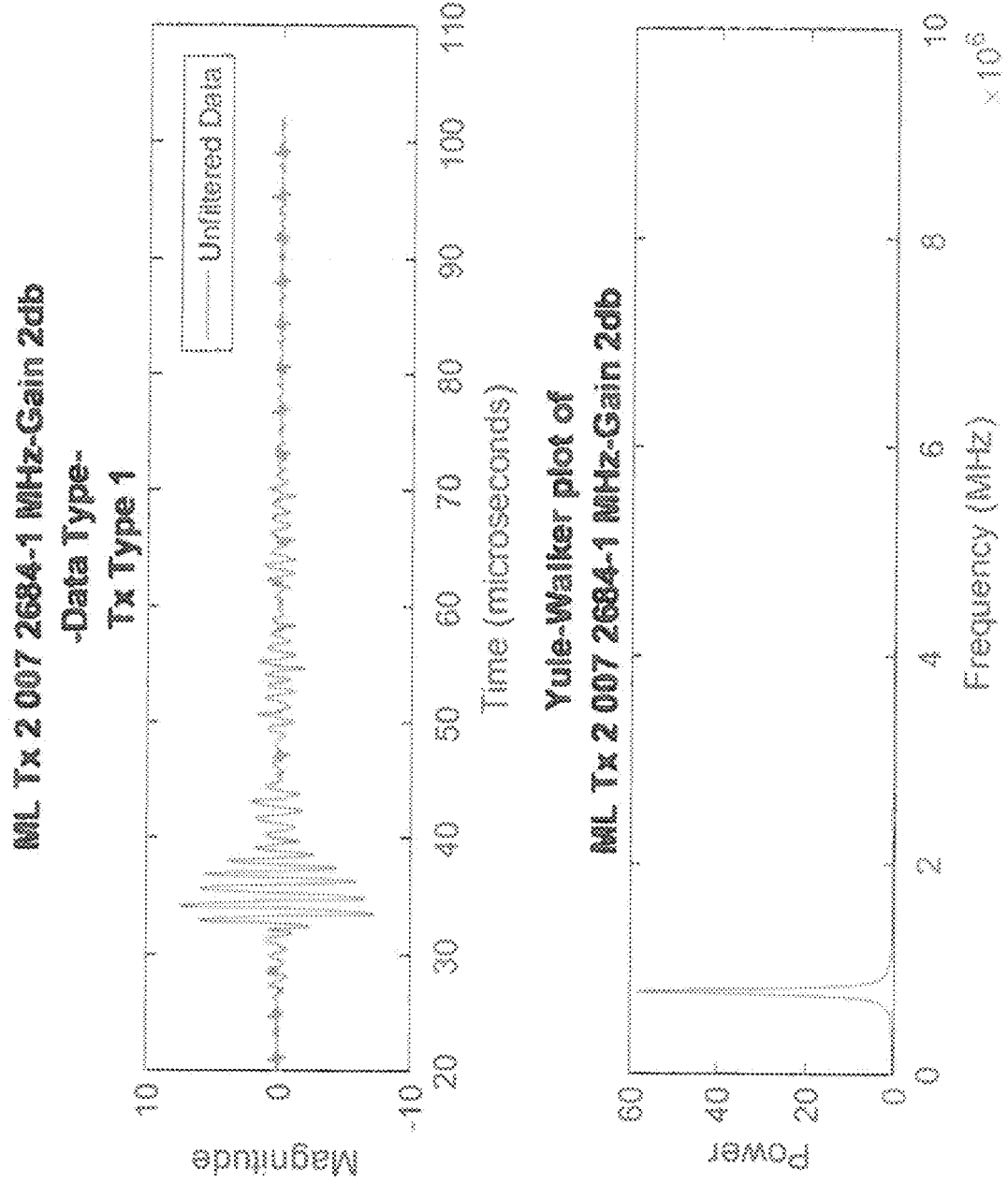
FIG. 26 is an example of a time domain and a frequency domain waveform for a TxRx Type 1 signal.
Figure 27:
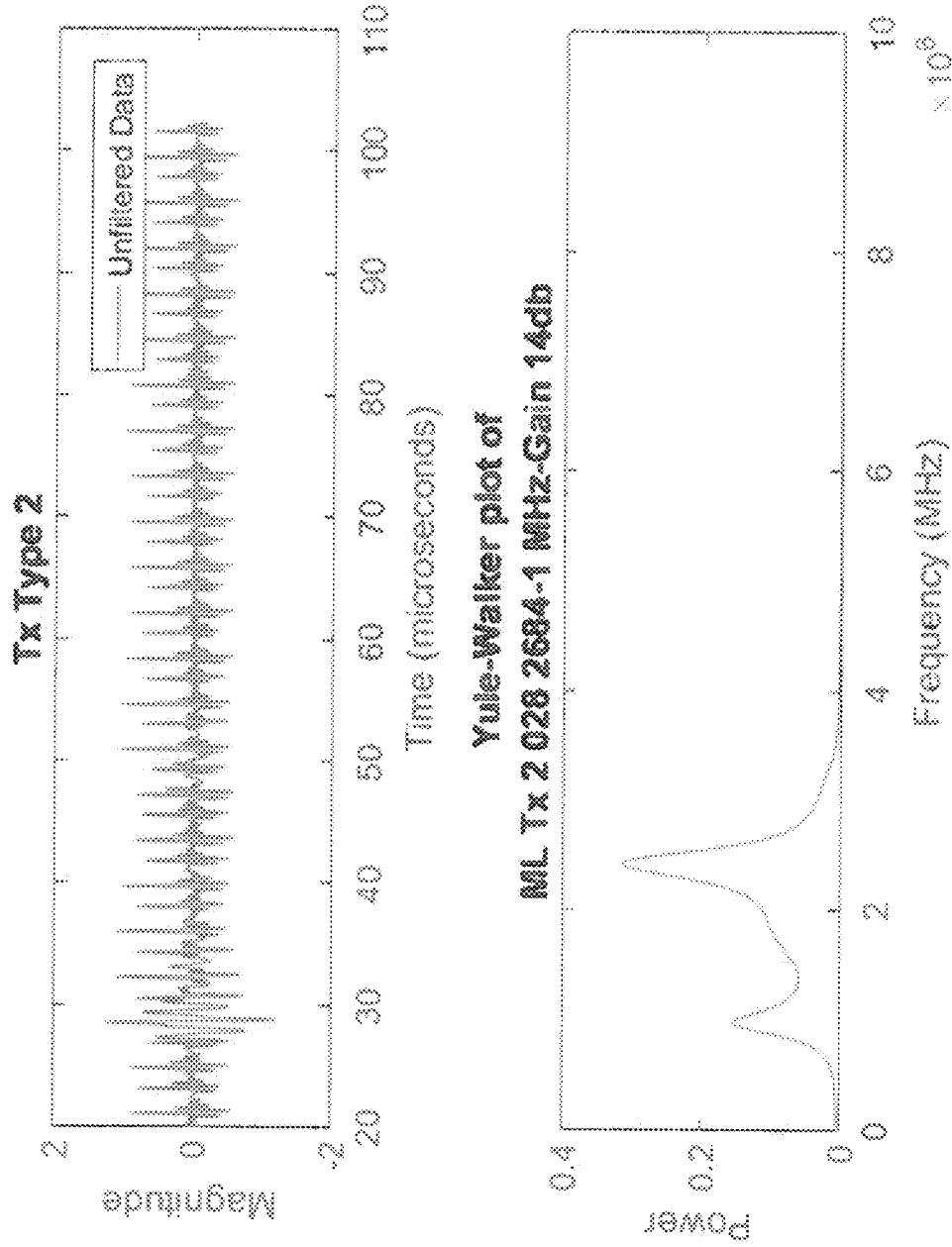
FIG. 27 is an example of a time domain and a frequency domain waveform for a TxRx Type 2 signal.
Figure 28:
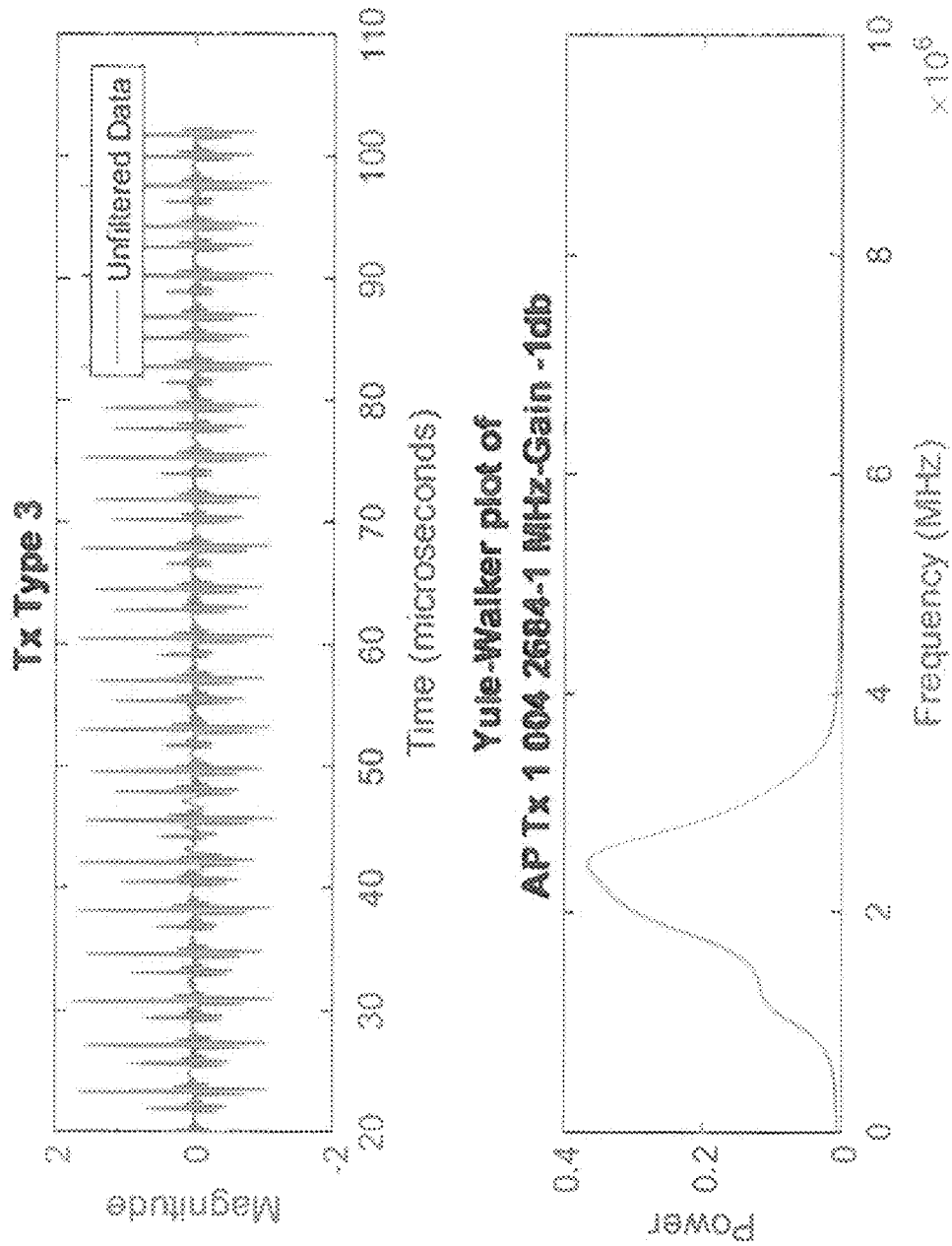
FIG. 28 is an example of a time domain and a frequency domain waveform for a TxRx Type 3 signal.
Figure 29:
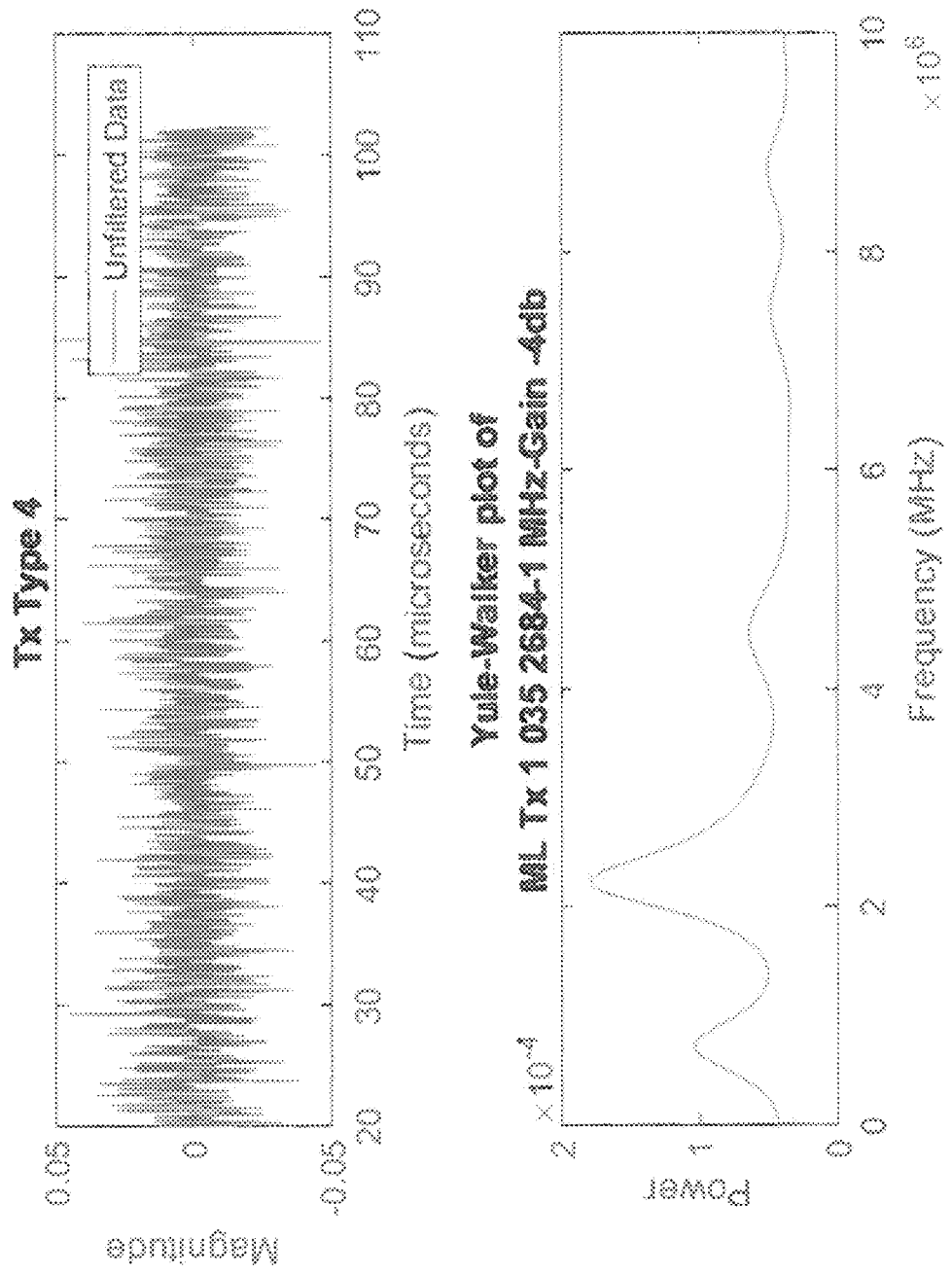
FIG. 29 is an example of a time domain and a frequency domain waveform for a TxRx Type 4 signal.

It is noted that the various embodiments of monitoring devices and systems, disclosed herein can be used as an alternative or replacement to traditional X-ray, or as a supplement to X-ray. A flow chart generally depicting one embodiment of a method 160 in which the monitoring devices and systems disclosed herein can be used in conjunction with X-ray is shown in FIG. 22. The sequence of steps discussed for FIG. 22 is for illustrative purposes only and is not meant to limit the method 160 in any way as it is understood that the steps may proceed in a different logical order, additional or intervening steps may be included, described steps may occur simultaneously, or described steps may be divided into multiple steps, without detracting from the invention.

After an injury or potential injury to a bone at 162, which may be due to trauma, surgery or other medical treatment, the bone is X-rayed at 164. The X-ray is reviewed by a clinician or medical practitioner at 166, who diagnoses the bone as broken or not broken.

If the bone is diagnosed as broken, the bone is fixated at 168, such as by applying an external fixator, such as a cast, or an internal fixator, such as a plate, screw, or nail. Other procedures for treating the broken bone can also be applied at 168. After the bone is fixated, the patient or clinician uses the monitoring device periodically, as indicated at 170, to monitoring the osteogenesis progress. A clinician can receive data from the monitoring device at 172, and assess whether the bone is still broken. If the bone is diagnosed as still broken, the patient and/or clinician can be updated at 174, and monitoring continues. For example, the monitoring may continue once daily or at another prescribed interval. If the bone is diagnosed as healed at 172, the fixation can be removed at 176. Thus, the removal of the fixation is determined using data from the monitoring device, rather than a fixed time frame as is currently conventional.

If the bone is diagnosed as not broken by the initial review of the X-ray at 166, the monitoring device can be used verify the diagnosis at 178. The patient or clinician uses the monitoring device, as indicated at 180, to generate data about the target site that is used by the clinician to assess whether the bone is broken at 180. If the bone is diagnosed as broken, the bone is fixated at 168, and the method continues as described above. If the bone is diagnosed as not broken at 180, the patient can be sent home at 182.

The method 160 has the advantages of reducing the number of X-rays a patient may have to undergo with an injury to a bone. Certain injuries, such as breaks to the femur or hip, currently may require many X-rays to determine how the break is healing. With the present method 160, a single X-ray may be used to make the initial diagnosis, and thereafter the monitoring device used to monitoring healing. The monitoring device has the advantage of being usable wherever is convenient for the patient.

FIGS. 30-41 illustrate one embodiment of a wavelet algorithm that may be used with the devices, systems, and methods described herein. Using the new wavelets and moving windows for power spectrum analysis, new patterns were observed in the data captured by a bone monitoring device as described above with reference to FIGS. 1-5, in reference to the previously described types of waveforms. The patient in this case was a sheep, and the healing of a surgical break to a bone in a leg of the sheep was monitored. For reference as used in FIGS. 30-41, the wavelet frequencies in accordance to their labels are as follows.

TABLE 1

| Wavelet Frequencies |
| --- |
| A9 = 19.5-0 kHz |
| D9 = 39-19.5 kHz |
| D8 = 78.125-19.5 kHz |
| D7 = 156.25-78.125 kHz |
| D6 = 312.5-156.25 kHz |
| D5 = 625-312.5 kHz |
| D4 = 1.25 MHz-625 kHz |
| D3 = 2.5-1.25 MHz |
| D2 = 5-2.5 MHz |
| D1 = 10-5 MHz |

Also for reference, the sliding scale window can produce up to three graphs based upon its scale. These are labeled as follows and are references to the told areas of the power spectrum: Maximum Power=Highest Power magnitude; Maximum Frequency=Frequency that had the Highest Power Value; and Mid Frequency=Frequency point that had 50% of the total power of the signal waveform. FIGS. 30-41 were all sampled from the 1 MHz frequency. It is noted that while the discussion with respect to FIGS. 30-39 generally references to Type 1, 2, 3, and 4, it is understood that Type 1 can apply to PE Type 1 and TxRx Type 1, Type 2 can apply to PE Type 2 and TxRx Type 2, and so on. While the plots selected for illustration are based on data from a TxRx sensor mode, the discussion of the types with respect to FIGS. 30-39 also applies for a PE sensor mode.

Type 1

With reference to FIG. 30, in the Wavelet analysis of the Type 1 waves, the largest amount of data was contributed by the D4 and D5 frequency ranges, together usually equaling more than 60-70% of the total data of the system. As this includes the 1 MHz range and the information just beneath it, this is to be expected. However, it is the magnitude of the D4 range that is to be noticed, as it is always the highest value and usually by a factor of two to three.

With reference to FIG. 31, in the moving window scale, the Maximum Power shows a greater surge where the first arriving signal forms, at least in the 15 microsecond window that is analyzed. This rapidly drops off as it moves past this signal, however. The Mid Frequency also has a noticeable jump at the beginning of the analysis waveform.

This was true for one example, shown in FIG. 31, and the similarly analyzed signal at a later date of healing, shown in FIG. 32-33, with enough changes to show both the similarities between the types of signals and the alteration in the healing of the bone.

These Type 1 signals could potentially be used as markers in later forms of analysis to judge the healing of the bones, as the Type 1 signals are the most reliable.

Type 2

With reference to FIG. 34, when analyzing the wavelets of the Type 2 waveforms, the D4 and D5 wave frequencies were both the most important for influencing the strength of the plot, but almost double the power was given to the D1 as well. Also, the difference between the D4 and D5 is much lower in the Type 2 waveforms than it is in Type 1 waveforms, enough to make them comparable to one another for Type 2. Also, their contribution in power to the total figure plot is much lower, usually between 30-50% of the data, rather than over half.

With reference to FIG. 35, also differing from the Type 1 waveforms, the Maximum Power of the moving window for Type 2 has either two noticeable lobes, or a very large one. This occurs in the same region roughly, between 30 to 60 microseconds, but with a very large dip in the center, usually between the 45 to 55 microsecond range. The Maximum Frequency, however, becomes much higher at the higher timepoints, usually enough to be four to five factors higher than the earlier values.

This was true in the data shown above, and repeated in the other waveforms analyzed, one example of which is shown in FIG. 36-37. Specifically, those with a matching type (i.e. Type 2). However, the data lacked the massive difference in the Maximum Power, instead showing only extreme plateaus in the Mid Frequency graph at the very beginning and end of the data set, with complete neutrality in the middle.

Type 3

With reference to FIG. 38, Type 3 data sets currently have a higher instance of being improperly analyzed, as they are usually classified as Type 2 or 4, but not Type 1, leaving the trending data unaffected. However, they are characterized by their extreme values shown in both wavelets and moving window functions. To begin with the wavelets, the D4 and D5 still have the higher values, but the D2 and D3 frequency range have much higher values, eclipsing those of the other frequencies. This is likely due to the non-attenuation of the waveforms, leading to constant high power.

With reference to FIG. 39, unlike the more complicated patterns in the moving windows of other types, the Mid Frequency and Maximum Power of the Type 3 waveforms are nigh constant, unsurprising given the consistency of the waveforms from beginning to end. It is important to note that these mid frequencies are also much lower than they were in the other frequency types, at least by the maximum points.

Type 4

With reference to FIG. 40, Type 4 is both the easiest to characterize and most random of the samples. It is random with very low magnitude, meaning that it is usually very different between samples. Wavelets have very consistent frequencies magnitudes between D1 through D6, meaning that there is both little attenuation or movement between the operating frequencies. This is to be expected, as the frequencies ranges generated are related to the sampling frequency, not the pulse frequency.

With reference to FIG. 41, the maximum frequency and mid frequency are much different. While the maximum frequency tends to have its higher values near the end, due to the required narrowing of the sampling window, the mid frequency appears to increase over the time window it is sampled at.

The wavelets and moving windows described for FIGS. 30-41 are one example of the wavelets and moving windows that can be used for the type classification and trend analysis described above, such as with respect to FIG. 5.

To the extent not already described, the different features and structures of the embodiments of the devices, systems, and methods disclosed herein may be used in combination with each other as desired. That one feature may not be illustrated in all of the embodiments is not meant to be construed that it cannot be, but is done for brevity of description. Thus, the various features of the different embodiments of the devices, systems, and methods related to osteogenic monitoring and stimulation may be mixed and matched as desired to form new embodiments, whether or not the new embodiments are expressly described.

The various embodiments of devices, systems, and methods provide improved monitoring, stimulation, and/or diagnosis of osteogenic conditions. In some applications, the devices, systems, and methods may be used after a fracture or break due to injury, or after a surgical procedure involving cutting or breaking a bone. In some applications, the devices, systems, and methods may be applied to distraction or bone regeneration.

The various embodiments of systems, methods, and other devices related to the invention disclosed herein provide improved osteogenic monitoring and/or stimulation. One advantage that may be realized in the practice of some embodiments of the described systems is the ability to quantitatively monitor and analyze bone healing or consolidation. Today, bone healing can be qualitatively monitored and analyzed using palpation and X-ray imaging. These previous procedures may be subjective and do not always accurately determine when a bone has fully consolidated. Using the various embodiments of systems, methods, and other devices disclosed herein, sensor data from a target site of a bone produces an objective, quantitative output.

Another advantage that may be realized in the practice of some embodiments of the described systems is that an osteogenesis stimulation treatment can be personalized, rather than fixed according to a generic treatment regimen. Such generic treatment regimen may be based on average healing times. For example, one current FDA-approved bone stimulation scheme uses a fixed frequency of 1.0 MHz pulses at 20 ms intervals. One session takes approximately 20 minutes, and multiple sessions are needed, regardless of the actual condition of the target site within the patient's bone. The systems, methods, and devices related to osteogenesis stimulation disclosed herein allow the treatment to be based on a real-time, quantified condition of the bone.

Yet another advantage that may be realized in the practice of some embodiments of the described systems is that the device for osteogenic monitoring and/or stimulation can be completely percutaneous and non-invasive.

Yet another advantage that may be realized in the practice of some embodiments of the described systems is that osteonecrosis and bone tumors may be accurately diagnosed, including whether the tumor is benign or malignant, in a non-invasive manner.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

What is claimed is:

1. A method of monitoring healing of a fracture in a bone, the method comprising:
   transmitting, from a first external ultrasound transducer applied on the skin of a patient, a plurality of signals that propagate in a transmission path transverse to a longitudinal axis of the bone at a location proximate to the fracture;
   capturing, by a receiver, the plurality of signals, after propagation of the plurality of signals in the transmission path through and about a target site of the bone that includes the fracture, to generate transducer readings;
   generating a plurality of digital signal packages containing digital signal data derived from the transducer readings;
   extracting time-domain features from the digital signal data in the plurality of digital signal packages;
   extracting frequency-domain features from the digital signal data in the plurality of digital signal packages;
   verifying a sensor mode from the time-domain features and/or the frequency-domain features that specifies whether the receiver is the first external ultrasound transducer or the receiver is a second external ultrasound transducer applied on the skin of the patient;
   classifying the digital signal data based on the sensor mode, characteristics of the time-domain features, and characteristics of the frequency-domain features into a first signal type and a second signal type;
   determining that the digital signal data of the first signal type is valid and that the digital signal data of the second signal type is invalid; and
   determining a healing state of the fracture based on the digital signal data of the first signal type,
   wherein the first plurality of signals are transmitted at a frequency in a range of 0.7 MHz to 3.0 MHz.

2. The method of claim 1, wherein the frequency is 1.0 MHz or 2.25 MHz.

3. The method of claim 1, wherein the first external ultrasound transducer is included in a monitoring device, and the monitoring device comprises a personal communications device or an annular band configured to be worn on the body of the patient.

4. The method of claim 3 further comprising:
   displaying the healing state on a display of the monitoring device or on a display remote from the monitoring device.

5. The method of claim 1 further comprising:
   setting the frequency of the first plurality of signals based on a pre-existing condition of the bone or a pre-existing condition of the patient.

6. The method of claim 1, wherein transmitting, from the first external ultrasound transducer applied on the skin of the patient, the first plurality of signals that propagate transverse to the longitudinal axis of the bone at the location proximate to the fracture comprises:
   transmitting, from the first external ultrasound transducer, a wave having a first frequency; and
   transmitting, from the first external ultrasound transducer, a wave having a second frequency.

7. The method of claim 6, wherein the first frequency is 1.0 MHz, and the second frequency is 2.25 MHz.

8. The method of claim 6, wherein the wave having the first frequency and the wave having the second frequency are simultaneously transmitted.

9. The method of claim 6, wherein the first frequency is different than the second frequency.

10. The method of claim 1, wherein the plurality of signals are captured at a plurality of gains.

11. The method of claim 10, wherein the plurality of gains differ from each other by 3 dB increments.

12. The method of claim 1, wherein the receiver is the first external ultrasound transducer, the plurality of signals are captured by the first external ultrasound transducer, and the sensor mode is a pulse-echo sensor modality.

13. The method of claim 1, wherein the receiver is the second external ultrasound transducer, the plurality of signals are captured by the second external ultrasound transducer, and the sensor mode is a transmit-receive sensor modality.

14. The method of claim 1 wherein determining the healing state of the fracture based on the digital signal data of the first signal type comprises:
   performing a time of flight analysis using the digital signal data of the first signal type; and
   performing an attenuation analysis using the digital signal data of the first signal type,
   wherein the healing state of the fracture is determined based on the time-domain features, the frequency-domain features, the time of flight analysis, and the attenuation analysis.

15. A bone monitoring device for monitoring healing of a fracture in a bone, the bone monitoring device comprising:
   a controller including a central processing unit and a memory, and the controller configured to:
      control a first skin-applied external ultrasound transducer to transmit a plurality of signals that propagate transverse to a longitudinal axis of the bone at a location proximate to the fracture;
      control a receiver to capture the plurality of signals, after propagation in the transmission path through a target site of the bone that includes the fracture, to generate transducer readings;
      generate a plurality of digital signal packages containing digital signal data derived from the transducer readings;
      extract time-domain features from the digital signal data in the plurality of digital signal packages;
      extract frequency-domain features from the digital signal data in the plurality of digital signal packages;
      verify a sensor mode from the time-domain features and/or the frequency-domain features that specifies whether the receiver is the first external transducer or the receiver is a second skin-applied external transducer;
      classify the digital signal data based on the sensor mode, characteristics of the time-domain features, and characteristics of the frequency-domain features into a first signal type and a second signal type;
      determine that the digital signal data of the first signal type is valid and that the digital signal data of the second signal type is invalid; and
      determine a healing state of the fracture based on the digital signal data of the first signal type,
      wherein the plurality of signals are transmitted at a frequency in a range of 0.7 MHz to 3.0 MHz.

16. The bone monitoring device of claim 15, wherein the receiver is the first external ultrasound transducer.

* * * * *